US011224418B2

(12) United States Patent
Bak-Boychuk et al.

(10) Patent No.: US 11,224,418 B2
(45) Date of Patent: Jan. 18, 2022

(54) PAPILLARY MUSCLE APPROXIMATION PADS

(71) Applicant: Edwards Lifesciences Corporation, Irvine, CA (US)

(72) Inventors: Gregory Bak-Boychuk, San Clemente, CA (US); Glen T. Rabito, Lake Forest, CA (US); Jesus Maria Cardenas, Huntington Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 140 days.

(21) Appl. No.: 16/388,715

(22) Filed: Apr. 18, 2019

(65) Prior Publication Data

US 2019/0380699 A1     Dec. 19, 2019

Related U.S. Application Data

(60) Provisional application No. 62/685,523, filed on Jun. 15, 2018.

(51) Int. Cl.
   *A61B 17/04*     (2006.01)
   *A61F 2/24*      (2006.01)
   *A61B 17/00*     (2006.01)

(52) U.S. Cl.
   CPC ........ *A61B 17/0469* (2013.01); *A61F 2/2457* (2013.01); *A61F 2/2466* (2013.01);
   (Continued)

(58) Field of Classification Search
   CPC ...... A61B 17/0469; A61B 2017/00862; A61B 2017/00867; A61B 2017/0406;
   (Continued)

(56) References Cited

U.S. PATENT DOCUMENTS 7,931,578 B2    4/2011   Whayne et al.
8,142,495 B2    3/2012   Hasenkam et al.
(Continued)

FOREIGN PATENT DOCUMENTS

WO    2007100268 A2    9/2007

OTHER PUBLICATIONS

Alloti et al., "Surgical approximation of the posterior papillary muscle in chronic ischemic mitral regurgitation—presentation of a new method of mitral valve repair," Journal of Cardiothoracic Surgery 2013, 8(Suppl 1):O268.
(Continued)

*Primary Examiner* — Brooke Nicole Labranche
(74) *Attorney, Agent, or Firm* — Chang & Hale LLP; Alan T. Hale

(57) ABSTRACT

A process for treating a heart valve involves delivering first and second working catheters to a ventricle of a heart of a patient using a transcatheter procedure, approximating a first pad associated with the first working catheter to a backside of a first papillary muscle of the ventricle, approximating a second pad associated with the second working catheter to a backside of a second papillary muscle of the ventricle, and manipulating one or more sutures physically coupled to at least one of the first and second pads to decrease a distance between the first and second papillary muscles.

19 Claims, 11 Drawing Sheets

(52) U.S. Cl.
CPC ............ *A61B 2017/00862* (2013.01); *A61B 2017/00867* (2013.01); *A61B 2017/0406* (2013.01); *A61B 2017/048* (2013.01); *A61B 2017/0414* (2013.01); *A61B 2017/0427* (2013.01); *A61B 2017/0464* (2013.01); *A61F 2210/0014* (2013.01); *A61F 2220/0091* (2013.01); *A61F 2230/0017* (2013.01)

(58) Field of Classification Search
CPC .... A61B 2017/0414; A61B 2017/0427; A61B 2017/0464; A61B 2017/048; A61F 2/2457; A61F 2/2466; A61F 2210/0014; A61F 2220/0091; A61F 2230/0017
See application file for complete search history.

(56) References Cited

U.S. PATENT DOCUMENTS

| | | | |
|---|---|---|---|
| 9,125,742 | B2 | 9/2015 | Yoganathan et al. |
| 2006/0287716 | A1 | 12/2006 | Banbury et al. |
| 2008/0228165 | A1* | 9/2008 | Spence ............... A61F 2/2466 604/510 |
| 2015/0025553 | A1 | 1/2015 | Del Nido et al. |
| 2015/0230919 | A1* | 8/2015 | Chau ................... A61F 2/246 623/2.11 |
| 2015/0359531 | A1 | 12/2015 | Sauer |

OTHER PUBLICATIONS

Isoda, S. "Papillary Muscle Approximation and Relocation with a Loop Technique for Mitral Complex Repair," General Thoracic and Cardiovascular Surgery, Jun. 2011, vol. 59, Issue 6, pp. 454-458.
Rama et al., "Papillary Muscle Approximation for Functional Ischemic Mitral Regurgitation", The Annals of Thoracic Surgery, 2007.
Wakasa et al., "The extent of papillary muscle approximation affects mortality and durability of mitral valve repair for ischemic mitral regurgitation," Journal of Cardiothoracic Surgery 2014, 9:98.
Yamauchi, H. "Right ventricular papillary muscle approximation as a novel technique of valve repair for functional tricuspid regurgitation in an ex vivo porcine model," J Thorac Cardiovasc Surg. Jul. 2012;144(1):235-42. doi: 10.1016/j.jtcvs.2012.01.028. Epub Feb. 16, 2012.

* cited by examiner

PAPILLARY MUSCLE APPROXIMATION PADS

CROSS-REFERENCE TO RELATED APPLICATION

This application claims priority to U.S. Provisional Application No. 62/685,523, filed Jun. 15, 2018, and entitled PAPILLARY MUSCLE APPROXIMATION PADS, the disclosure of which is hereby incorporated by reference in its entirety.

BACKGROUND

Field

The present disclosure generally relates to the field of valve correction.

Description of Related Art

Heart valve dysfunction can result in regurgitation and other complications due to valve prolapse from failure of valve leaflets to properly coapt. For atrioventricular valves, papillary muscle position can affect the ability of valve leaflets to function properly.

SUMMARY

In some implementations, the present disclosure relates to a method for treating a heart valve. The method comprises delivering first and second working catheters to a ventricle of a heart of a patient using a transcatheter procedure, approximating a first pad associated with the first working catheter to a backside of a first papillary muscle of the ventricle, approximating a second pad associated with the second working catheter to a backside of a second papillary muscle of the ventricle, and manipulating one or more sutures physically coupled to at least one of the first and second pads to decrease a distance between the first and second papillary muscles.

In some embodiments, the method further comprises engaging the first pad with the first papillary muscle using an engagement feature of the first pad and engaging the second pad with the second papillary muscle using an engagement feature of the second pad. For example, the engagement feature of the first pad comprises one or more barbs configured to protrude outward from the first pad and at least partially embed in tissue of the first papillary muscle.

The first pad can comprise a rigid frame disposed at least partially within a pledget form. For example, the frame may be associated with one or more barbs that are at least partially exposed through the pledged form. In some embodiments, the method further comprises articulating the first pad to engage tissue of the backside of the first papillary muscle using the first working catheter. For example, the method may further comprise releasing the first pad from the first working catheter using a release wire associated with the first working catheter.

In some embodiments, the method further comprises tying the one or more sutures at a physical location external to the patient, wherein the one or more sutures are connected between the ventricle and the physical location external to the patient via an artery of the patient. The one or more sutures can comprise a first suture threaded through a suture-holding feature of the first pad, and, a second suture threaded through a suture-holding feature of the second pad.

The method may further comprise tying a first end of the first suture to a first end of the second suture. For example, said tying the first end of the first suture to the first end of the second suture is performed outside of a body of the patient. Manipulating the one or more sutures may comprise pulling one or more of a second end of the first suture and a second end of the second suture to draw the first and second papillary muscles together. The method may further comprise delivering the first working catheter and the second working catheter to an atrium of the heart via a steerable sheath using a transseptal procedure.

In some implementations, the present disclosure relates to a tissue-engagement pad comprising an at least partially rigid frame, one or more suture-holding features associated with the frame, a cushion cover surrounding at least a portion of the frame, and one or more barbs associated with the frame that protrude at least partially through the cushion cover.

The frame may comprise memory metal. In some embodiments, the frame has an elongated rhombus shape. In some embodiments, the frame is compressible. The cushion cover may comprise one or more suture holes. For example, the tissue-engagement pad may comprise a suture passing through the one or more suture holes.

In some embodiments, the frame comprises one or more suture-holding features. The frame may comprise an articulation feature configured to allow the frame to pivot about a pivot point. For example, the articulation feature may be configured to engage an articulation wire or rod. In some embodiments, the tissue-engagement pad further comprises one or more hinge features. The one or more barbs may be configured to be articulated away from the frame.

In some implementations, the present disclosure relates to a papillary muscle binding system comprising a delivery catheter, a papillary muscle cuff, a delivery rod disposed at least partially within the delivery catheter and coupled to the papillary muscle cuff, and a suture threaded through one or more suture holes associated with the papillary muscle cuff. The papillary muscle binding system may further comprise an articulation mechanism associated with the delivery rod and a frame of the papillary muscle cuff.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

DETAILED DESCRIPTION

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview

In humans and other vertebrate animals, the heart generally comprises a muscular organ having four pumping chambers, wherein the flow thereof is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.).

Figure 1:
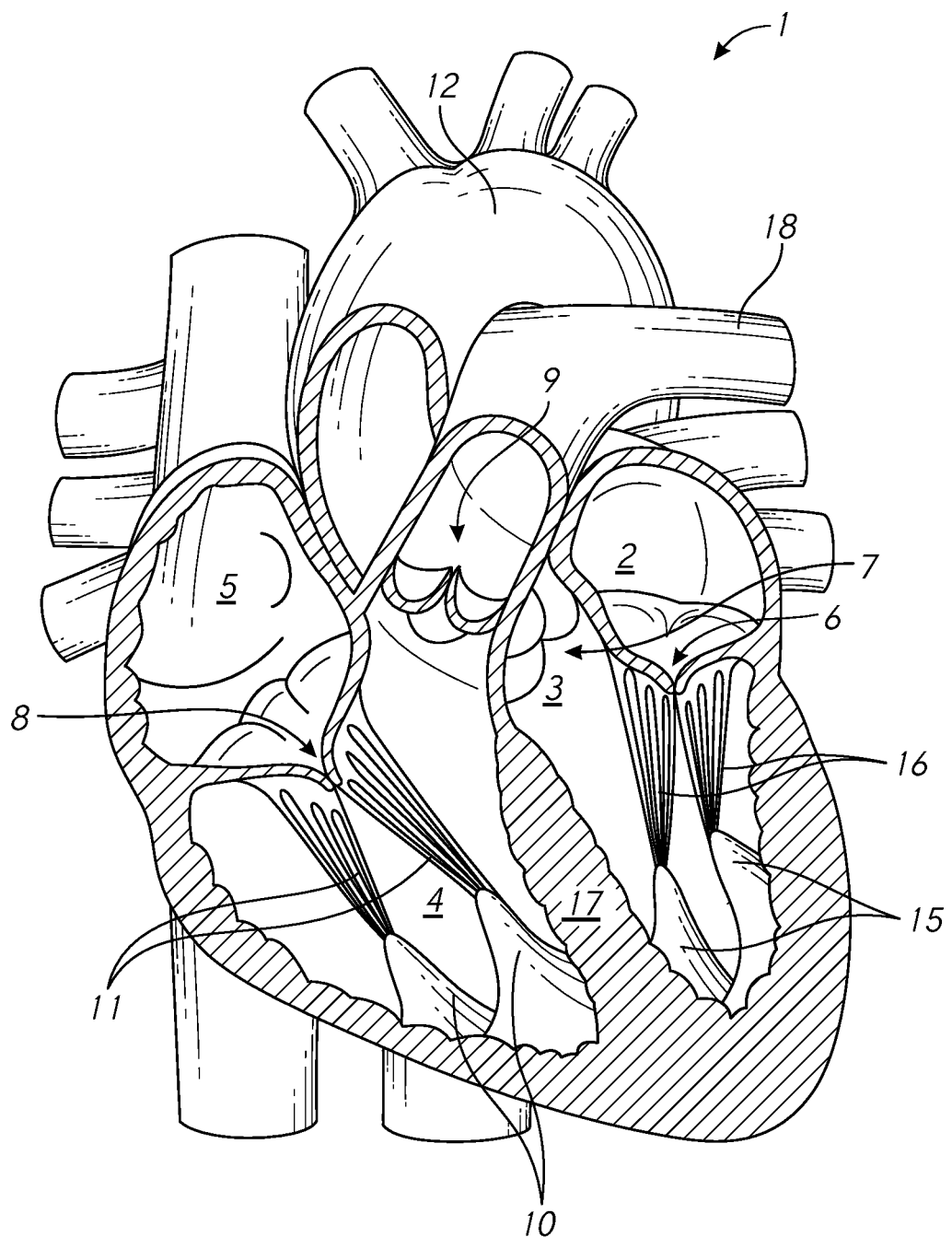
FIG. 1 provides a cross-sectional view of a human heart.

FIG. 1 illustrates an example representation of a heart 1 having various features relevant to certain embodiments of the present disclosure. The heart 1 includes four chambers, namely the left atrium 2, the left ventricle 3, the right ventricle 4, and the right atrium 5. A wall of muscle 17, referred to as the septum, separates the left 2 and right 5 atria and the left 3 and right 4 ventricles. The heart 1 further includes four valves for aiding the circulation of blood therein, including the tricuspid valve 8, which separates the right atrium 5 from the right ventricle 4. The tricuspid valve 8 may generally have three cusps or leaflets and may generally close during ventricular contraction (i.e., systole) and open during ventricular expansion (i.e., diastole). The valves of the heart 1 further include the pulmonary valve 9, which separates the right ventricle 4 from the pulmonary artery 11 and may be configured to open during systole so that blood may be pumped toward the lungs, and close during diastole to prevent blood from leaking back into the heart from the pulmonary artery. The pulmonary valve 9 generally has three cusps/leaflets, wherein each one may have a crescent-type shape. The heart 1 further includes the mitral valve 6, which generally has two cusps/leaflets and separates the left atrium 2 from the left ventricle 3. The mitral valve 6 may generally be configured to open during diastole so that blood in the left atrium 2 can flow into the left ventricle 3, and advantageously close during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

Heart valves may generally comprise a relatively dense fibrous ring, referred to herein as the annulus, as well as a plurality of leaflets or cusps attached to the annulus. Generally, the size of the leaflets or cusps may be such that when the heart contracts the resulting increased blood pressure produced within the corresponding heart chamber forces the leaflets at least partially open to allow flow from the heart chamber. As the pressure in the heart chamber subsides, the pressure in the subsequent chamber or blood vessel may become dominant and press back against the leaflets. As a result, the leaflets/cusps come in apposition to each other, thereby closing the flow passage.

The atrioventricular (i.e., mitral and tricuspid) heart valves may further comprise a collection of chordae tendineae and papillary muscles for securing the leaflets of the respective valves to promote and/or facilitate proper coaptation of the valve leaflets and prevent prolapse thereof. The papillary muscles, for example, may generally comprise finger-like projections from the ventricle wall. With respect to the tricuspid valve 8, the normal tricuspid valve may comprise three leaflets (two shown in FIG. 1) and three corresponding papillary muscles 10 (two shown in FIG. 1). The leaflets of the tricuspid valve may be referred to as the anterior, posterior and septal leaflets, respectively. The valve leaflets are connected to the papillary muscles by the chordae tendineae 11, which are disposed in the right ventricle 4 along with the papillary muscles 10. Although tricuspid valves are described herein as comprising three leaflets, it should be understood that tricuspid valves may occur with two or four leaflets in certain patients and/or conditions; the principles relating to papillary muscle adjustment disclosed herein are applicable to atrioventricular valves having any number of leaflets and/or papillary muscles associated therewith.

The right ventricular papillary muscles 10 originate in the right ventricle wall, and attach to the anterior, posterior and septal leaflets of the tricuspid valve, respectively, via the chordae tendineae 11. The papillary muscles 10 of the right ventricle 4 may have variable anatomy; the anterior papillary may generally be the most prominent of the papillary muscles. The papillary muscles 10 may serve to secure the leaflets of the tricuspid valve 8 to prevent prolapsing of the leaflets into the right atrium 5 during ventricular systole. Tricuspid regurgitation can be the result of papillary dysfunction or chordae rupture.

With respect to the mitral valve 6, a normal mitral valve may comprise two leaflets (anterior and posterior) and two corresponding papillary muscles 15. The papillary muscles 15 originate in the left ventricle wall and project into the left ventricle 3. Generally, the anterior leaflet may cover approximately two-thirds of the valve annulus. Although the anterior leaflet covers a greater portion of the annulus, the posterior leaflet may comprise a larger surface area in certain anatomies.

The valve leaflets of the mitral valve 6 may be prevented from prolapsing into the left atrium 2 by the action of the chordae tendineae 16 tendons connecting the valve leaflets to the papillary muscles 15. The relatively inelastic chordae tendineae 16 are attached at one end to the papillary muscles 15 and at the other to the valve leaflets; chordae tendineae from each of the papillary muscles 15 are attached to a respective leaflet of the mitral valve 6. Thus, when the left ventricle 3 contracts, the intraventricular pressure forces the valve to close, while the chordae tendineae 16 keep the leaflets coapting together and prevent the valve from opening in the wrong direction, thereby preventing blood to flow back to the left atrium 2. The various chords of the chordae tendineae may have different thicknesses, wherein relatively thinner chords are attached to the free leaflet margin, while relatively thicker chords (e.g., strut chords) are attached farther away from the free margin.

The present disclosure provides systems devices and methods for implementing percutaneous papillary muscle approximation and/or ventricular reshaping, which may be used or implemented for the purpose of treating functional mitral regurgitation (FMR), tricuspid regurgitation, and/or other cardiac defect or condition. In some implementations, papillary muscle approximation in accordance with the present disclosure utilizes one or more pad or pledget devices, as described in detail below.

Generally, functional mitral regurgitation (FMR) may be considered a disease or condition of the left ventricle of the heart. Functional mitral regurgitation may be developed, for example, after or in connection with myocardial infarction or coronary artery disease. In connection with various heart conditions, as a portion of the heart loses blood supply, one or more ventricles of the heart, such as the left ventricle, may dilate, causing displacement of one or more papillary muscles disposed therein. Such papillary muscle displacement may cause or affect leaflet tethering, loss of coaptation, and/or a regurgitant flow path. Although certain embodiments are disclosed herein in the context of left ventricular papillary muscle adjustment or manipulation, it should be understood that the principles disclosed herein are applicable to the right ventricle, and associated anatomy and conditions.

In some implementations, embodiments of the present disclosure provide for treatment for patients suffering from infarction on the inferior wall of the ventricle(s). Such patients may suffer from relatively limited annular dilation, but significant dilation of the inferior wall, causing the posteromedial papillary muscle(s) to distend laterally and/or apically. Distention of the papillary muscle(s) can result in a regurgitant jet or flow at or near the medial scallop (P3) of the posterior leaflet of the mitral valve. Certain embodiments disclosed herein advantageously provide a subvalvular solution for mitral regurgitation through papillary muscle approximation, which may be suitable due to the relatively limited annular dilation that may be experienced by patients suffering from myocardial infarction. The terms "approximation" and "papillary muscle approximation" are used herein according to their broad and/ordinary meanings and may refer to the manipulation or adjustment of a papillary muscle to bring the papillary muscle in closer proximity to another papillary muscle or anatomy of the heart.

In some implementations, papillary muscle approximation can be performed surgically. Papillary muscle approximation procedures may provide for at least partial reduction in left (and/or right) ventricular volume, reduction in recurrent mitral regurgitation, and/or other improvement in cardiac function. However, with respect to surgical solutions, such surgeries may be relatively difficult to teach and/or perform. Therefore, it may be desirable to implement papillary muscle approximation through percutaneous approaches, which may provide access to therapy treating the underlying cause of functional mitral regurgitation to increased numbers of patients and/or physicians.

Figure 2:
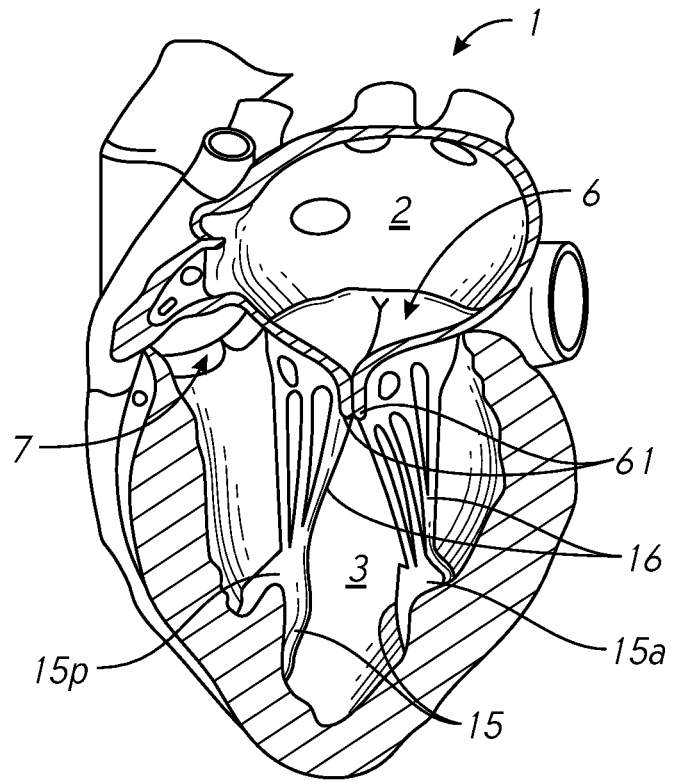
FIG. 2 provides a cross-sectional view of the left ventricle and left atrium of an example heart.

FIG. 2 provides a cross-sectional view of the left ventricle 3 and left atrium 2 of an example heart 1. The diagram of FIG. 2 shows the mitral valve 6, wherein the disposition of the valve 6, papillary muscles 15 and/or chordae tendineae 16 may be illustrative as providing for proper coapting/coaptation of the valve leaflets 61 to advantageously at least partially prevent regurgitation and/or undesirable flow into the left atrium from the left ventricle 3, and vice versa. Although a mitral valve 6 is shown in FIG. 2 and various other figures provided herewith, and described herein in the context of certain embodiments of the present disclosure, it should be understood that papillary muscle adjustment principles disclosed herein may be applicable with respect to any atrioventricular valve and/or associated anatomy (e.g., papillary muscles, chordae tendineae, trabeculae carneae, ventricle wall, etc.), such as the tricuspid valve.

As described above, with respect to a healthy heart valve as shown in FIG. 2, the valve leaflets 61 may extend inward from the valve annulus and come together in the flow orifice to permit flow in the outflow direction (e.g., the downward direction in FIG. 2) and prevent backflow or regurgitation in the inflow direction (e.g., the upward direction in FIG. 2). For example, during atrial systole, blood flows from the atrium 2 to the ventricle 3 down the pressure gradient, resulting in the chordae tendineae 16 being relaxed due to the atrioventricular valve 6 being forced open. When the ventricle 3 contracts during ventricular systole, the increased blood pressures in both chambers may push the valve 6 closed, preventing backflow of blood into the atria 2. Due to the lower blood pressure in the atria compared to the ventricles, the valve leaflets may tend to be drawn toward the atria. The chordae tendineae 16 can serve to tether the leaflets and hold them in a closed position when they become tense during ventricular systole. The papillary muscles 15 provide structures in the ventricles for securing the chordae tendineae and therefore allowing the chordae tendineae to hold the leaflets in a closed position. The papillary muscles 15 may include an anterolateral papillary muscle 15a, which may be tethered to the posterior leaflet, for example, and a posteromedial papillary muscle 15p, which may be tethered to the anterior leaflet, for example. With respect to the state of the heart 1 shown in FIG. 2, the proper coaptation of the valve leaflets, which may be due in part to proper position of the papillary muscles 15, may advantageously result in mitral valve operation substantially free of leakage.

Heart valve disease represents a condition in which one or more of the valves of the heart fails to function properly.

Figure 3:
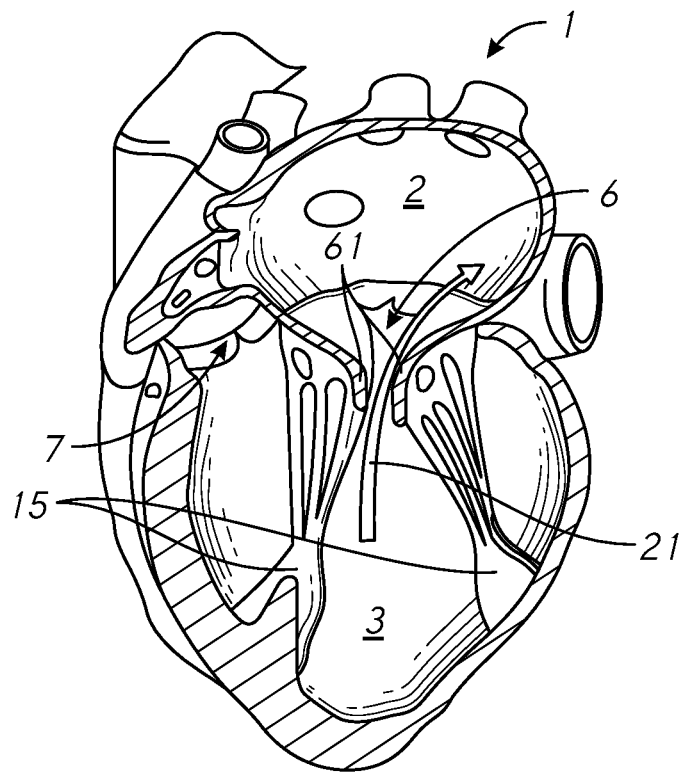
FIG. 3 provides a cross-sectional view of a heart experiencing mitral regurgitation.

Diseased heart valves may be categorized as stenotic, wherein the valve does not open sufficiently to allow adequate forward flow of blood through the valve, and/or incompetent, wherein the valve does not close completely, causing excessive backward flow of blood through the valve when the valve is closed. In certain conditions, valve disease can be severely debilitating and even fatal if left untreated. With regard to incompetent heart valves, over time and/or due to various physiological conditions, the position of papillary muscles may become altered, thereby potentially contributing to valve regurgitation. For example, as shown in FIG. 3, which illustrates a cross-sectional view of a heart 1 experiencing mitral regurgitation flow 21, dilation of the left ventricle may cause changes in the position of the papillary muscles 15 that allow flow 21 back from the ventricle 3 to the atrium 2. Dilation of the left ventricle can be caused by any number of conditions, such as focal myocardial infarction, global ischemia of the myocardial tissue, or idiopathic dilated cardiomyopathy, resulting in alterations in the geometric relationship between papillary muscles and other components associated with the valve(s) that can cause valve regurgitation. Functional regurgitation may further be present even where the valve components may be normal pathologically yet may be unable to function properly due to changes in the surrounding environment. Examples of such changes include geometric alterations of one or more heart chambers and/or decreases in myocardial contractility. In any case, the resultant volume overload that exists as a result of an insufficient valve may increase chamber wall stress, which may eventually result in a dilatory effect that causes papillary muscle alteration resulting in valve dysfunction and degraded cardiac efficiency.

With further reference to FIG. 3, the heart 1 is shown in a state where functional mitral valve regurgitation is present. Functional mitral valve regurgitation may be considered a disease of the left ventricle 3, rather than of the mitral valve 6. For example, mitral valve regurgitation may occur when the left ventricle 3 of the heart 1 is distorted or dilated, displacing the papillary muscles 15 that support the two valve leaflets 61. The valve leaflets 61 therefore may no longer come together sufficiently to close the annulus and prevent blood flow back into the atrium 2. If left untreated, the functional mitral valve regurgitation experienced in the state shown in FIG. 3 may overload the heart 1 and can possibly lead to or accelerate heart failure. Solutions presented herein provide devices and methods for moving the papillary muscles 15 closer to their previous position, which may advantageously reduce the occurrence of mitral regurgitation.

As shown in FIG. 3, the leaflets 61 of the mitral valve (or tricuspid valve) are not in a state of coaptation, resulting in an opening between the mitral valve leaflets 61 during the systolic phase of the cardiac cycle, which allows the leakage flow 21 of fluid back up into the atrium 2. The papillary muscles 15 may be displaced due to dilation of the left ventricle 3, or due to one or more other conditions, as described above, which may contribute to the failure of the valve 6 to close properly. The failure of the valve leaflets 61 to coapt properly may result in unwanted flow in the outflow direction (e.g., the upward direction in FIG. 3) and/or unwanted backflow or regurgitation toward the inflow direction (e.g., the downward direction in FIG. 2).

Certain embodiments disclosed herein provide solutions for incompetent heart valves that involve papillary muscle re-positioning and/or approximation. Solutions presented herein may be used to at least partially change the position of one or more papillary muscles in order to reduce the occurrences and/or severity of regurgitation, such as mitral regurgitation. Mitral valve regurgitation often may be driven by the functional/physical positioning changes described above, which may cause papillary muscle displacement and/or dilatation of the valve annulus. As the papillary muscles move away from the valve annulus, the chordae tendineae connecting the muscles to the leaflets may become tethered. Such tethering may restrict the leaflets from closing together properly, either symmetrically or asymmetrically, depending on the relative degree of displacement between the papillary muscles. Moreover, as the annulus dilates in response to chamber enlargement and increased wall stress, increases in annular area and changes in annular shape may increase the degree of valve insufficiency.

Various techniques that suffer from certain drawbacks may be implemented for treating mitral valve dysfunction, including surgical repair or replacement of the diseased valve or medical management of the patient. Medical management may be appropriate or effective primarily in early stages of mitral valve dysfunction, during which levels of regurgitation may be relatively low. For example, such medical management may generally focus on volume reductions, such as diuresis or afterload reducers, such as vasodilators, for example. Valve replacement operations may also be used to treat regurgitation from valve dysfunction. However, such operations can result in ventricular dysfunction or failure following surgery. Further limitations to valve replacement solutions may include the potential need for lifelong therapy with powerful anticoagulants in order to mitigate the thromboembolic potential of prosthetic valve implants. Moreover, in the case of biologically-derived devices, such as those used as mitral valve replacements, the long-term durability may be limited.

Another commonly employed repair technique involves the use of annuloplasty rings to improve mitral valve function. An annuloplasty ring may be placed in the valve annulus and the tissue of the annulus sewn or otherwise secured to the ring. Annuloplasty rings can provide a reduction in the annular circumference and/or an increase in the leaflet coaptation area. However, annuloplasty rings may flatten the saddle-like shape of the valve and/or hinder the natural contraction of the valve annulus. In addition, various surgical techniques may be used to treat valve dysfunction. However, such techniques may suffer from various limitations, such as requiring opening the heart to gain direct access to the valve and the valve annulus. Therefore, cardiopulmonary bypass may be required, which may increase morbidity and mortality to the surgical procedures. Additionally, for surgical procedures, it can be difficult or impossible to evaluate the efficacy of the repair prior to the conclusion of the operation.

Disclosed herein are devices and methods for treating valve dysfunction without the need for cardiopulmonary bypass and without requiring major remodeling of the dysfunctional valve. In particular, passive techniques to change the shape and/or position of the papillary muscles are disclosed for reducing regurgitation while maintaining substantially normal leaflet anatomy. Furthermore, various embodiments disclosed herein provide treatments of valve dysfunction that can be executed on a beating heart, thereby allowing for the ability to assess the efficacy of the papillary muscle re-positioning treatment and potentially implement modification thereto without the need for bypass support.

With respect to percutaneous approaches or solutions for papillary muscle approximation, certain anatomy of the ventricular chamber may present certain challenges with respect to the navigation of papillary muscle approximation and/or engagement/anchoring tools or devices therein. Such anatomy can make the securing of papillary muscles and/or means or mechanisms for approximating or bringing the play muscles together relatively challenging. For example, papillary muscle shape, size, and/or the number of heads or forms associated with papillary muscles may vary from patient-to patient. Devices and methods for ventricular reshaping may therefore advantageously utilize delivery systems and implant devices designed to navigate the complex inner anatomy of the ventricle.

In some implementations, the present disclosure provides devices and methods for eliminating or reducing mitral regurgitation at least in part by reducing left ventricular volume and/or relieving leaflet tethering via papillary muscle approximation. Such devices/methods may advantageously utilize tissue-contact pad devices or mechanisms. Although certain surgical procedures may be implemented for papillary muscle approximation, as described above, embodiments of the present disclosure advantageously provide for percutaneous access to the papillary muscles and/or associated anatomy, which may be safer and/or easier to execute relative to certain surgical procedures, and therefore may allow for a relatively greater number or percentage of potential patients to be eligible for valve treatment through papillary muscle approximation.

Percutaneous Papillary Muscle Approximation

Certain embodiments disclosed herein provide systems, devices and methods for adjusting the position of papillary muscles in the left and/or right ventricles of a heart in order to improve valve coaptation during ventricular systole. For example, in some implementations, the present disclosure relates to percutaneous subvalvular implants for the left or right ventricle that are designed to at least partially reduced mitral regurgitation by relieving leaflet tethering via papillary muscle approximation using pad-like pledgets, which may comprise relatively small forms of cotton or other relatively soft material in an at least partially flat pad shape, on the outsides of the papillary muscles. By drawing the pads/pledgets inward, the papillary muscles can be brought together. Therefore, systems, devices, and methods for percutaneous papillary muscle approximation in accordance with the present disclosure can be implemented for the purpose of heart valve dysfunction (e.g., functional mitral regurgitation, as described above). Such systems, devices, and methods may implement one or more pads or pad-type forms for applying inward pressure to papillary muscles in a ventricle of the heart.

As referenced above, functional mitral regurgitation may be considered a disease associated with the left ventricle of the heart. Although certain solutions are disclosed herein in the context of mitral regurgitation, it should be understood that principles disclosed herein are applicable with respect to other types of valve dysfunction, such as tricuspid valve dysfunction. Therefore, description herein of mitral valve correction, and/or left ventricular anatomy are applicable to corresponding anatomy of, for example, the right ventricle and/or tricuspid valve, or other valve or anatomy.

In some situations, functional mitral regurgitation may be developed after, or in connection with, a myocardial infarction, or in patients suffering from coronary artery disease. For example, as a portion of the heart loses blood supply in connection with cardiac dysfunction, the left (or right) ventricle may become dilated, which may result in the at least partial displacement of one or more papillary muscles within the ventricle. Such papillary muscle displacements may cause leaflet tethering through connection with the papillary muscles via chordae tendineae, which may result in relative loss of coaptation of the associated valve leaflets, allowing for a regurgitant flow path between the valve leaflets.

Embodiments disclosed herein provide for the treatment of functional mitral regurgitation and/or other cardiac conditions through the approximation or re-positioning of papillary muscles, which may reduce leaflet tethering, thereby allowing for proper coaptation of valve leaflets. Papillary muscle approximation/re-positioning in accordance with the present disclosure may advantageously reduce left ventricular volume through the application of force on the ventricular wall via connection with the papillary muscle(s). Furthermore, systems, devices and methods disclosed herein may provide papillary muscle approximation that prevents further papillary muscle dislocation and/or subsequent leaflet tethering.

In some implementations, valve correction in accordance with the present disclosure may be particularly suited for treatment of functional mitral regurgitation patients suffering from infarctions on, for example, the inferior ventricular wall. Generally, such patients may have relatively limited annular dilation with respect to the dysfunctional heart valve but may suffer from relatively significant dilation of the inferior wall, which may cause the posteromedial papillary muscle to distend laterally and/or apically. Distention of the papillary muscle(s) can result in the formation of a regurgitant jet within gap(s) between the leaflets of the valve. For example, regurgitation may occur primarily at or around the medial third scallop (i.e., "P3") of the posterior leaflet of the mitral valve. Embodiments disclosed herein advantageously provide subvalvular approaches for resolving or treating mitral regurgitation or other valve dysfunction. Where relatively minor annular dilation is present, subvalvular approaches in accordance with the present disclosure may directly address the causes of functional mitral regurgitation in some patients, and therefore may alone be sufficient to resolve or improve mitral regurgitation conditions.

Various subvalvular techniques may be implemented to treat functional mitral regurgitation through papillary muscle approximation or relocation. However, where such techniques are surgical in nature, they may prove relatively invasive and/or difficult to perform or teach. For example, in some implementations, pledget-type pads may be sutured directly to the papillary muscle(s) via an aortotomy, or directly through the mitral valve. The papillary muscles may be completely approximated, wherein the pledget-type pads are sutured together to lock the papillary muscles in a closed, approximated position. In an alternative implementation, a Gore-Tex tube or the like may be used to encircle and approximate the papillary muscles. The native trabeculae carneae may be used to help keep the tube positioned at or near/about the base of the papillary muscle(s). Although the above-referenced techniques for approximating papillary muscles may result in reduction in mitral regurgitation, percutaneous solutions and techniques in accordance with embodiments of the present disclosure may generally be less invasive by nature, and therefore desirable in certain situations.

Embodiments disclosed herein provide for the use of pad devices configured to be placed against, and apply pressure to, papillary muscles to approximate and/or otherwise adjust positioning of the papillary muscles. In some embodiments, the pads are configured to engage with the papillary muscle tissue to resist pull out forces that may be experienced by the papillary muscle(s) during ventricular contraction and/or dilation. Pads positioned behind respective papillary muscles may be tied to one another and/or the ventricular anatomy such as to apply inward force to the papillary muscles that exceeds lateral displacement forces, thereby allowing for the pads to serve as valve-correction implants in the ventricle. The term "pad" is used herein according to its broad and/ordinary meaning and may describe a structure or device having any shape or form configured to have force applied thereto, wherein such force is at least partially distributed over a surface area of the pad. Pads in accordance with the present disclosure may comprise pledgets, straps, cuffs, balls, or the like.

Figure 4:
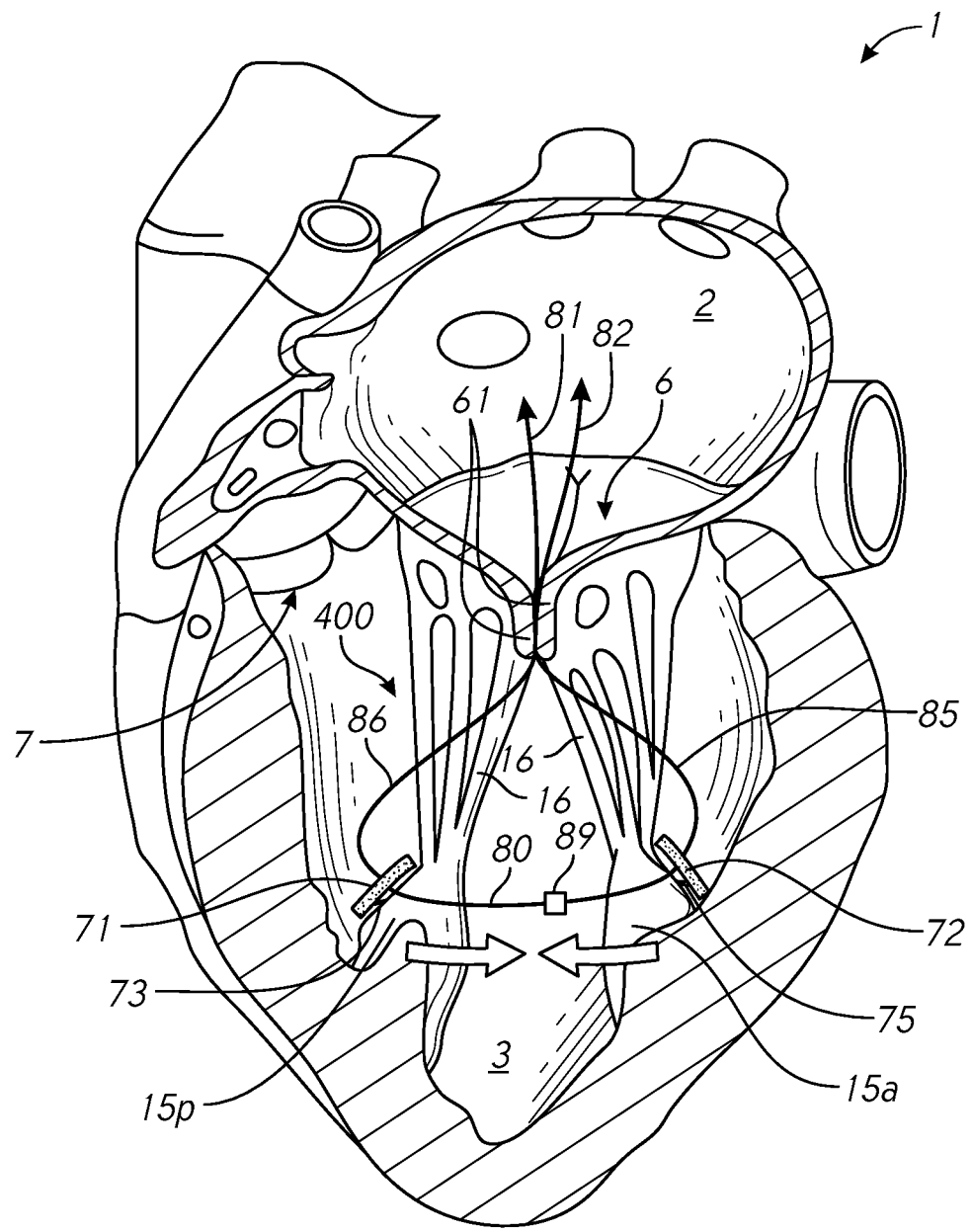
FIG. 4 illustrates a cross-section of a heart having a papillary muscle adjustment system disposed therein according to one or more embodiments.

FIG. 4 illustrates a cross-sectional view of a ventricle 3 of a heart 1 having implanted therein one or more papillary muscle approximation pads 71, 72 coupled by a coupling means 80, such as a suture, tie, strap, or the like. The papillary muscle approximation assembly 400, which includes the illustrated pads 71, 72 may serve to reduce or eliminate regurgitation (e.g., mitral regurgitation) of the valve 6 at least in part by reducing ventricular volume (e.g., left ventricular volume) and/or relieving leaflet tethering generally caused by the displacement/positioning of the papillary muscle(s) (e.g., 15a and/or 15p), which may pull on the valve leaflets 61 via connecting structures 16, referred to as chordae tendineae. Papillary muscle approximation forces are applied in the ventricle 3 by the approximation assembly 400 using the pledget-type pads 71, 72. The papillary muscle approximation assembly 400 may be implanted in the ventricle 3 using a percutaneous approach, which may be preferable to surgical implantation of papillary muscle approximation assemblies or devices, which may require open-chest operation and/or cardiopulmonary bypass. The relatively lesser impact of percutaneous implantation in accordance with the present disclosure relative to open-chest surgical operation may advantageously increase the number of patients that may be considered suitable candidates for papillary muscle approximation.

The pads 71, 72 may comprise any suitable or desirable material. For example, in some embodiments, the pads 71, 72 comprise cotton or other relatively soft material. The pads 71, 72 may be implanted or positioned behind respective papillary muscles via percutaneous delivery. Once the pads 71, 72 are fixed to the respective papillary muscles 15p, 15a, one or more sutures 80 coupling the pads 71, 72 may be tightened and/or fixed/secured, such that the papillary muscles remain in an approximated position, wherein the papillary muscles are drawn towards one another from an initial laterally-displaced position. For example, as described above, relative lateral displacement of papillary muscles may be caused at least in part by ventricular dilation.

The pads 71, 72 and/or suture(s) 80 may be delivered to their respective implanted positions within the ventricle using one or more mechanical tools configured to navigate the respective components around the papillary muscles to their target locations. Such mechanical delivery tools are described in detail below in connection with FIGS. 5-11. For example, it may be necessary to drive the pads 71, 72 around their respective target papillary muscles and dig or engage the pad(s) into the tissue of the papillary muscle(s). By cinching and/or otherwise increasing the tension of the suture(s) 80 between the pads 71, 72, the distance between the papillary muscles may be shortened, such that the papillary muscles become approximated to one another.

In some implementations, the proximal suture portion(s) 81, 82 may be tightened and/or tied outside of the body. For example, by pulling on one or both of the proximal suture portions 81, 82, the tension of the suture(s) 80 coupling the pads 71, 72 may be increased or tightened, thereby drawing the papillary muscles closer together. Although the proximal portions 81, 82 are illustrated in the atrium 2, it should be understood that description herein related to proximal suture portions of a papillary muscle approximation assembly may be at least partially disposed or accessible external to the body during at least a portion of an implantation procedure. For example, the proximal suture portions 81, 82 may be accessible through percutaneous access, such as through a transcatheter access.

The suture portions 85, 86 may be cinched or locked together using a cinching or locking mechanism 89, such as a clip-type or other locking mechanism. For example, the cinching or locking mechanism 89 may be used to bring the two suture portions 85, 86 together, and secure the suture portions relative to one another. Therefore, once the cinching/locking mechanism 89 is used to achieve a desired tension between the pad devices 71, 72, the cinching/locking mechanism 89 may be used to hold the desired tension between the pad devices 70, 72. As the cinching/locking mechanism 89 is drawn closer to the pads 71, 72, it may increase the tension between the pads and draw the pads, and therefore the associated papillary muscles, inward. In some implementations, the cinching functionality may be controlled or executed at least in part from outside the body. Therefore, embodiments of the present disclosure may advantageously provide for suture tension and/or cinching/locking management, or action affecting tension between the implanted pads 71, 72, from outside the body, at least in part.

Figures 5A, 5B:
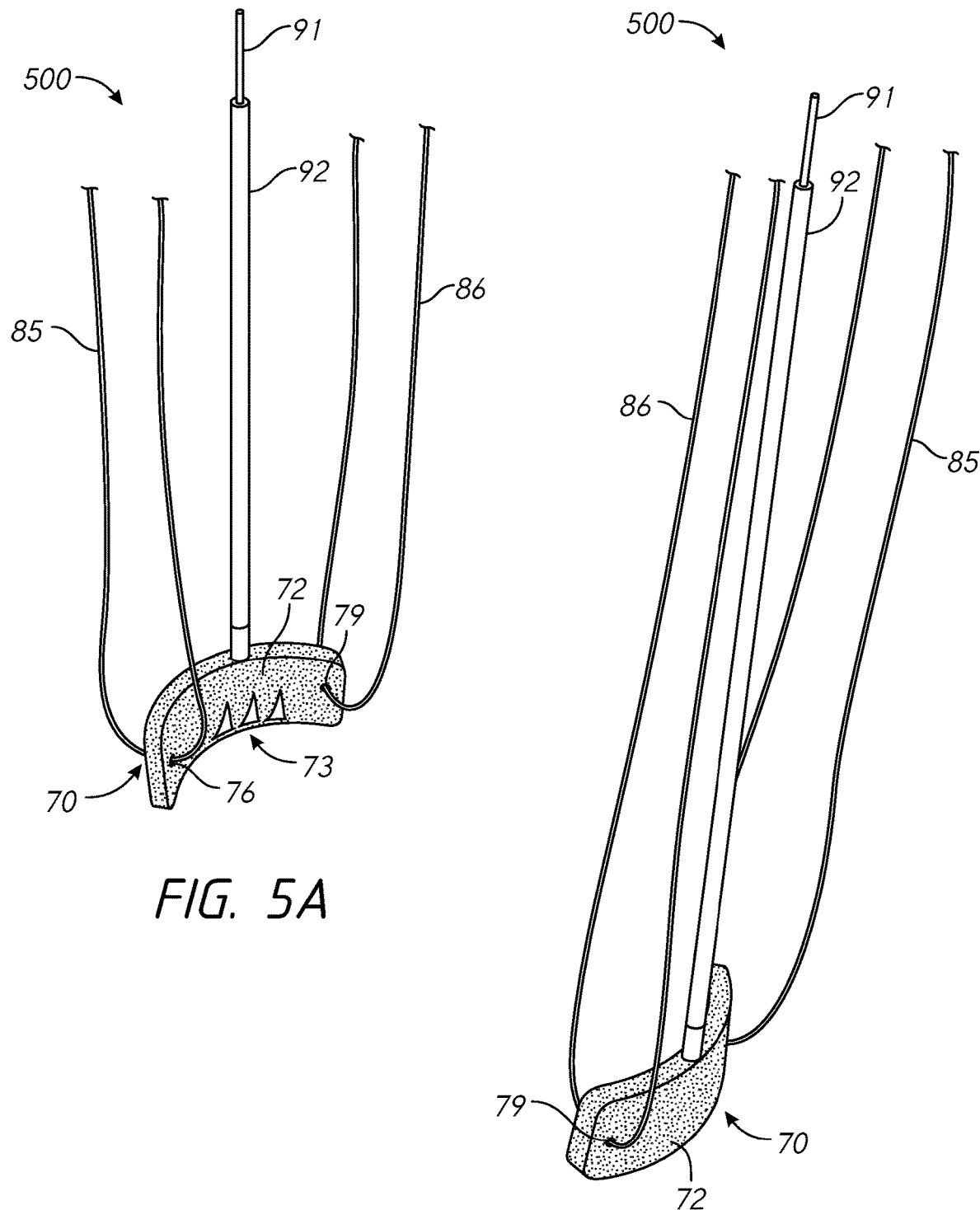
FIGS. 5A and 5B provide front and back perspective views, respectively, of a tissue adjustment pad delivery assembly in accordance with one or more embodiments.

Papillary muscle approximation pads in accordance with the present disclosure may be delivered to the target ventricle using a catheter-based delivery system. FIGS. 5A and 5B provide perspective views of a pad-type tissue adjustment delivery system 500 in accordance with one or more embodiments. The system 500 includes a pledget pad 70 that is coupled to, or otherwise associated with, a delivery catheter 92, which may be configured to articulate the pad 70. Furthermore, the pad 70 may comprise tissue-engaging barbs 73 for securing the pad 70 to a target papillary muscle. The pad 70 may be designed and configured to be secured behind a papillary muscle, or other ventricular tissue, and tied to another pad (not shown) using one or more sutures attached to the pad(s). The delivery system 500 may be delivered to the ventricle using a trans-catheter procedure.

The delivery system 500 may further be configured to navigate and/or articulate the pad 70 within the target ventricle using an articulation mechanism or subsystem. The pad 70 may comprise articulatable or non-articulatable barb features 73, a compressible at least partially rigid (e.g., metal or memory metal) frame (not shown), and/or one or more suture holes 76, 79 for threading suture line around and/or through the pad 70. The internal (or external) frame may be oblong- or diamond-shaped in some embodiments. In certain embodiments, the frame may be secured to a backside of the pad 70.

The pad 70 comprises one or more barbs 73 that may be actuatable using the delivery catheter 92, or component thereof, for engagement with the tissue at the implantation site. Suture lines 85, 86 are threaded through the suture holes 76, 79 of the pad or frame. In some implementations, the sutures are tied together outside the body during implantation of the pad 70.

The pad 70 may comprise an internal frame (not shown) that is at least partially covered or encapsulated with a covering. Although certain embodiments are described herein comprising an internal frame, it should be understood that some embodiments of pads in accordance with the present disclosure do not include an internal frame component. Furthermore, while certain embodiments are described as having an internal frame that is covered with a covering, or the like, it should be understood that in some implementations or embodiments, a papillary muscle approximation pad device may comprise a frame or other rigid component or structure that is externally coupled to the pad or covering.

The frame or structure of the device 70 may be associated with one or more articulation features, which may advantageously allow for percutaneous delivery of the pad device 70 to the target location. For example, the frame or structure (not shown) may have one or more holes, grooves, apertures, or the like for holding or guiding sutures 85, 86. As shown in the diagrams of FIGS. 5A and 5B, the tissue contact covering portion 72 of the pad device 70 may further comprise one or more holes, grooves, apertures, or other passageways or features designed or configured to allow for threading therethrough of a suture (e.g., 85, 86).

In certain embodiments, the pad device 70 and/or associated frame may comprise one or more barbs 73, or other tissue anchoring component(s), which may be configured to facilitate engagement of the pad device 70 with biological tissue, such as tissue of a papillary muscle. In some embodiments, such tissue-engagement feature 73 may be controllable using an actuator component 91, which may be controllable external to the body when the pad device 70 is being implanted.

The papillary muscle approximation pad delivery assembly 500 may advantageously allow for relatively less invasive percutaneous delivery of the pad device 70, wherein the ability to deliver the pad 70 percutaneously may be facilitated at least in part by the shape and/or configuration of the frame (not shown; e.g., memory metal frame) within or otherwise associated with the pad device 70. Furthermore, the relatively soft covering 72 of the pad 70 may comprise pledget-type material, which may be relatively soft and less destructive to ventricular tissue compared to certain metallic anchors or implants.

During implantation, the pad 70 may be placed at least partially behind a papillary muscle. The assembly 500 comprises a working catheter 92, which may provide sufficient structure or rigidity for advancing the pad 70 around and/or behind a papillary muscle. In the illustrated embodiment, two separate suture portions 85, 86 are shown as being associated with respective sides or portions of the pad 70. Although separate suture portions 85, 86 are shown coupled to separate ends or portions of the pad 70, it should be understood that in some embodiments implementations, a single suture may be threaded through both holes or apertures 76, 79. During implantation, proximal portions of the sutures 85, 86 may be accessible outside of the body, such as through a transcatheter access providing access to the target ventricle through a blood vessel access point for the operation. Although FIGS. 5A and 5B illustrate views of a single papillary muscle approximation pad delivery system 500, when implementing papillary muscle approximation, two or more pads may be implanted behind respective papillary muscles. Such pads may be implanted using separate delivery systems.

The pad device 70 may have associated therewith one or more anchors, such as micro anchors, that are configured or designed to be at least partially embedded into the target tissue, such as papillary muscle tissue. Engagement of the anchor feature 73 may help to prevent the implanted pad 70 from riding up the papillary muscle in response to tension for force applied thereto.

In some embodiments, the frame and covering of the pad 70 are configured to allow for the pad 70 to be fit into a relatively small catheter. For example, the pad and/or frame may be configured to assume a compressed or collapsed state when within the catheter 92 and expand once deployed from the catheter. Such functionality may be facilitated through the use of a memory metal frame.

The pad 70, and/or covering thereof, may advantageously provide a relatively large or broad surface area for tissue contact, wherein the load applied to the pad 70 when the pad is pulled inward towards the center of the ventricle is distributed relatively widely over the surface area of the contact surface. The distribution of force over the broad surface area of the pad 70 may advantageously prevent blood flow from being obstructed or pinched-off in such a way as to prevent proper blood flow. That is, overly-narrow constriction of the pad 70 may result in damage to the local tissue. Therefore, the shape and/or surface area of the pad 70 may be such as to not sufficiently obstruct blood flow in the papillary muscle when approximation force is applied thereto.

As referenced above, the pad device 70 may comprise one or more tissue engagement feature 73, such as barbs or the like. Such features may be integrated or associated with a frame of the pad device 70. In some implementations, the tissue engagement feature 73 is configured to be maintained in a retracted state, such that the tissue engagement feature(s) 73 do not substantially protrude away from the body of the pad device 70 when the pad is being advanced and/or positioned within the ventricle. The retractability of the tissue engagement feature 73 may allow for navigation of the pad device 70 within the ventricle without the tissue engagement features 73 becoming entangled with anatomy of the ventricle and/or otherwise damaging or undesirably contacting tissue of the ventricle that is not the target engagement tissue for the device 70. The assembly 500 may therefore comprise a mechanism for maintaining the tissue engagement feature(s) 73 in a retracted or tilted-in state, wherein the tissue-engagement feature(s) may be extended outward, or tilted forward, to engage the target tissue when proximate thereto. The tissue engagement feature(s) 73 may comprise any number, shape, or size of tissue-engagement features. Furthermore, such features may comprise teeth, barbs, micro-barbs, pins, anchors, or the like. The tissue engagement feature actuator 91 may be used to selectively protrude or retract the tissue engagement feature(s) 73. For example, in some implementations, by pulling the actuator component 91, the tissue engagement feature(s) 73 (e.g., barbs) may be extended outward away from the pad 70.

Figure 6:
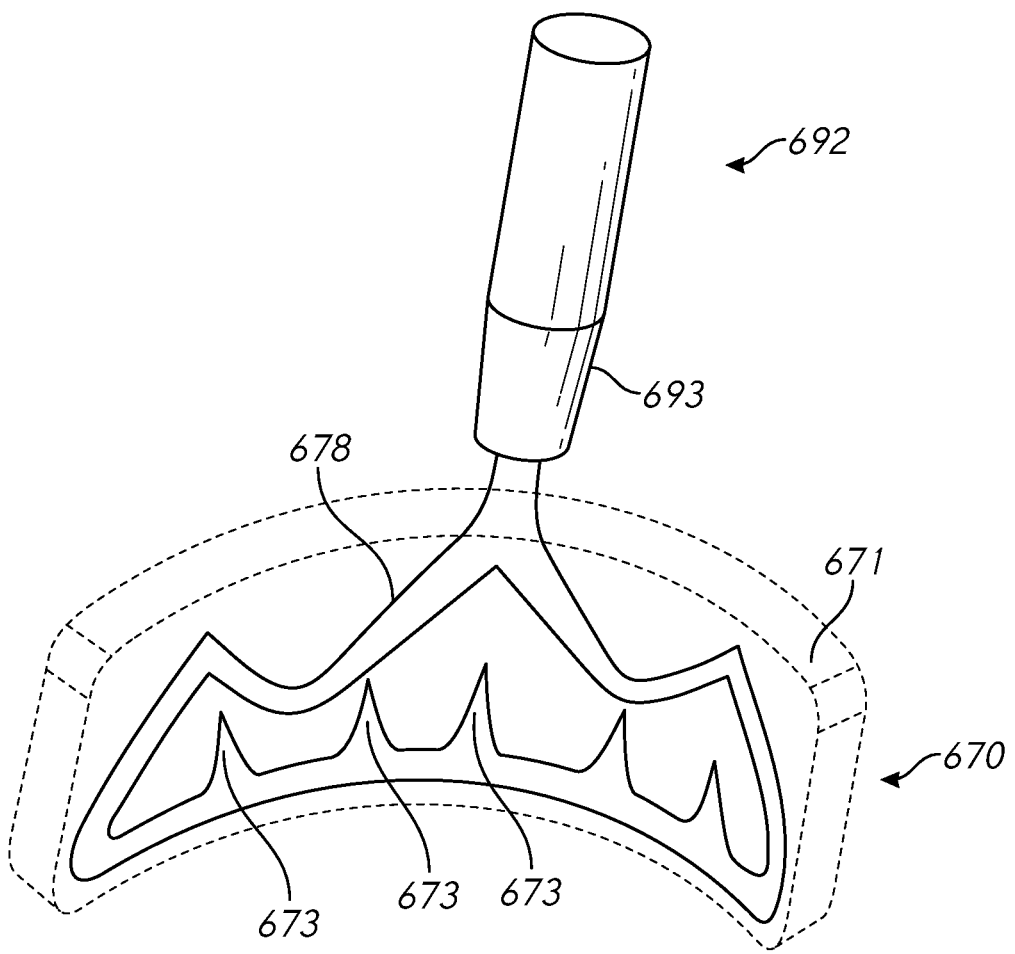
FIG. 6 illustrates a tissue adjustment pad device having a frame associated therewith in accordance with one or more embodiments.

FIG. 6 illustrates a tissue adjustment pad device 670 having a frame 678 associated therewith in accordance with one or more embodiments. The inner frame 678 has a plurality of actuatable barbs associated therewith. The pad device 670 comprises an outer pledget cover 671 configured to make the pad relatively less destructive to tissue within the ventricle compared to metallic anchors or implants that may be used with other tissue reshaping/relocating devices. The barbs 673 of the frame 678 are shaped for grabbing the papillary muscle tissue through the cover 671. The articulation of the frame 678 may be achieved using the delivery catheter 692.

The embodiment of FIG. 6 shows the frame 678 disposed at least partially within or behind the tissue contact pad or covering 671. In some embodiments, the frame 678 comprises memory metal or other at least partially rigid material. The covering 671 may comprise cloth, or other relatively soft or non-abrasive material designed to distribute force over an area of tissue without substantially damaging or constricting tissue or anatomy associated therewith. The pad device 670 may be associated with, or coupled to, the deployment catheter 692. In some embodiments, a release wire or other feature may be used to control the protrusion and/or retraction of the tissue engagement features 673 associated with frame 678, as described in detail above. For example, where the tissue engagement features 673 comprise barbs or teeth, in some embodiments, such barbs/teeth may be coupled to or associated with a single plane or structure, wherein rotation or movement of the structure may cause the barbs/teeth to move outward or inward together. That is, a single actuator action may be used to protrude or retract a plurality of tissue engagement features in some embodiments. By providing torque on the associated actuator structure, the position of the tissue engagement features may be controlled.

Figure 7:
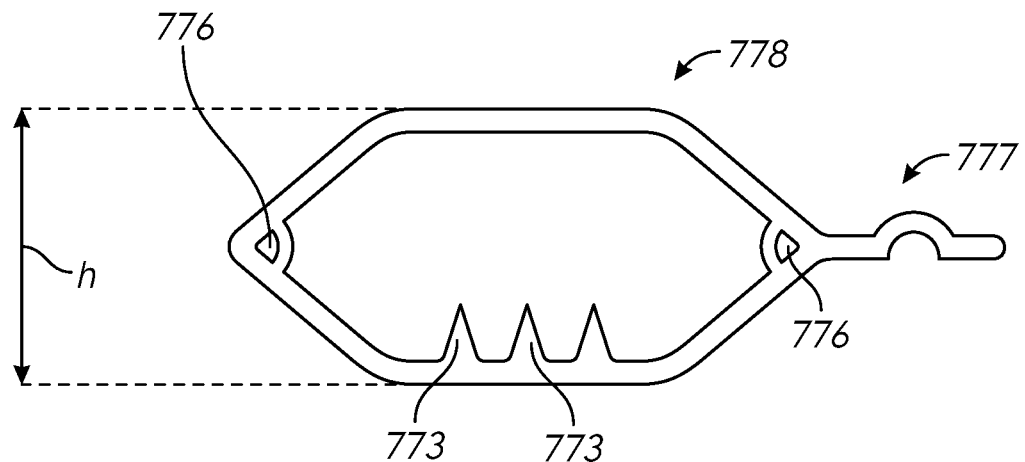
FIG. 7 illustrates a frame for a tissue adjustment device in accordance with one or more embodiments.
Figure 8:
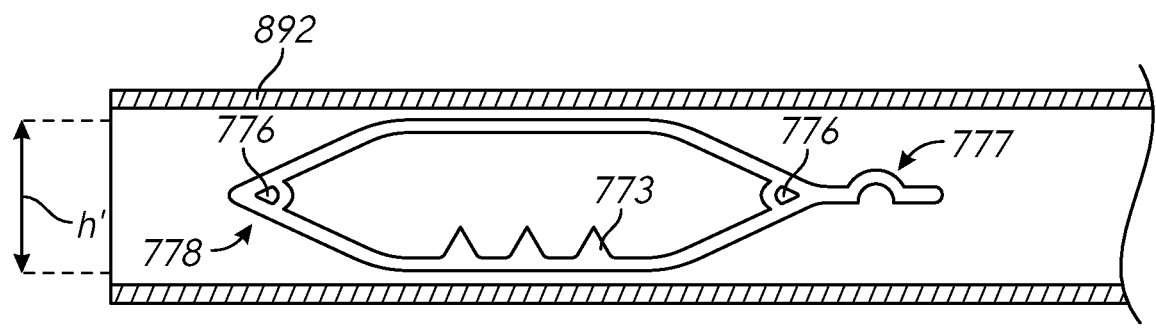
FIG. 8 illustrates the frame of FIG. 8 in a collapsed state within a catheter in accordance with one or more embodiments.
Figure 9A:
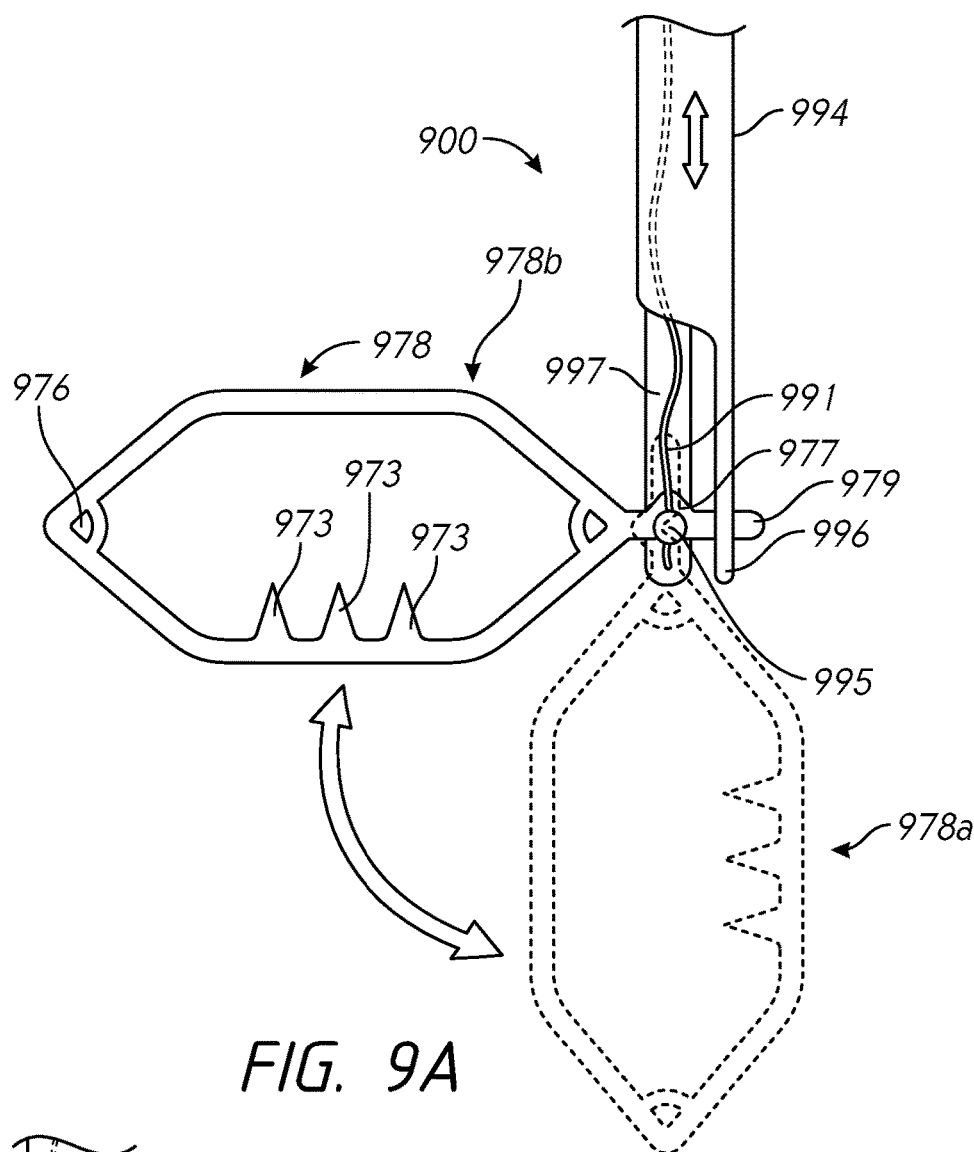
FIGS. 9A and 9B provide front and side views, respectively, of a frame articulation system in accordance with one or more embodiments.
Figure 9B:
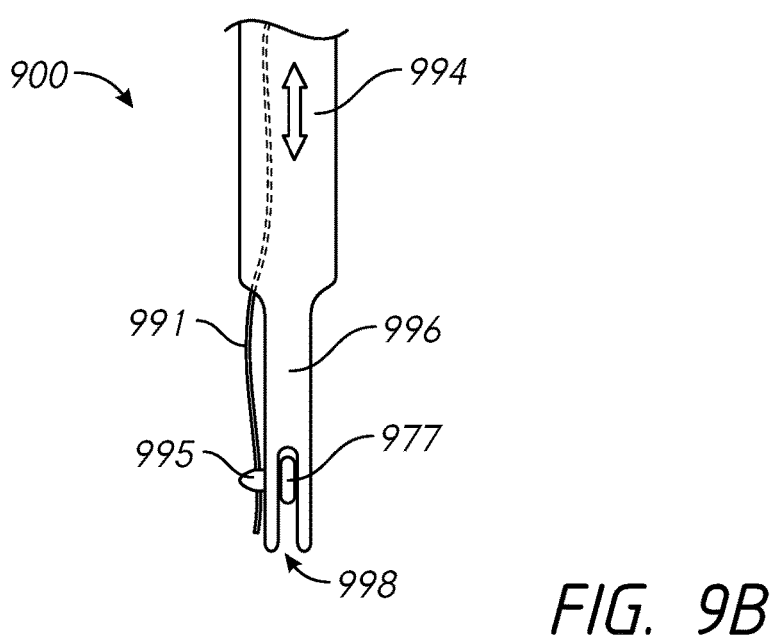

FIG. 7 illustrates a frame 778 for a tissue-adjustment pad device in accordance with one or more embodiments. As described above, a pledget-type cover may encapsulate a frame in some embodiments of a papillary muscle contact pad. The frame 778 is illustrated in FIGS. 7 and 8 without a tissue contact pad or cover for simplicity, and it should be understood that a cover and/or pad may at least partially cover, or be attached to, the frame 778. The frame may comprise, for example, memory metal (e.g., Nitinol), and may include one or more articulation features to allow for percutaneous delivery. In certain embodiments, the frame 778 has one or more holes 776 for sutures, barbs 773 for pad engagement, and a hinge shaft 777. The frame 778 may further have an oblong or diamond shape that facilitates delivery in, and/or deployment from, a catheter. In certain embodiments, a release wire may be used to control disengagement of the frame 777 from a delivery catheter. While FIG. 7 illustrates the frame 778 in an expanded form, FIG. 8 shows the frame 778 in a compressed form within a delivery catheter 892.

In some embodiments, the frame 778 further comprises a hinge shaft feature 777, which may be configured to cooperate with a release wire feature (not shown) to control disengagement of the frame 778 from the delivery catheter. The frame 778 may comprise memory metal (e.g., Nitinol), or other at least partially rigid material, and may serve to provide structural support for a tissue-contact cover or pad (not shown). The pivot hinge feature 777 may be associated with a side of the frame, which may advantageously allow for articulation about the pivot hinge member 777. Articulation of the frame 778, may advantageously allow for navigation of the frame 778 within a heart ventricle and around a papillary muscle. The frame 778 may be, for example, laser-cut.

The pivot hinge feature 777 may be configured to be coupled to, or disposed on or about, a pivot pin, such that the frame 778 may be selectively held at a desired angle with respect to the delivery catheter hinge pin (not shown), which may allow for navigation of the frame 778 around or behind the papillary muscle. In some embodiments, the frame 778 comprises one or more suture holes or apertures 776.

FIG. 8 shows the frame 778 and a collapsed or compressed state within a delivery catheter 892. The diagram of FIG. 8 shows how the oblong or diamond shape of the frame 778 can facilitate transport thereof to the target location in the delivery catheter 892.

FIGS. 9 A and 9B illustrate a frame 978, which may be similar in certain respects to the frame 778 shown in FIGS. 7 and 8 described above. For convenience, the frame 987 is illustrated without a pad covering, although it should be understood that the frame 987 may be covered by, or attached to, a relatively soft cover as described in detail herein. The frame 978 is shown in first 978a and second 978b positions. Frame articulation may be achieved using the delivery catheter 994 and the frame 978, and in particular the hinge shaft 977, 979.

The frame 978 may be configured to fit about a pivot pin feature 995 of the catheter assembly 994, such that the frame 978 may be configured to be in a longitudinal position 978a when initially deployed from the catheter 994, and further rotated to an orthogonal or angled orientation 978b for positioning behind a papillary muscle. For example, the frame 978 may be maintained initially within the catheter 994 in the straight longitudinal position 978a, and subsequently rotated upward with respect to the orientation of FIG. 9A to allow for fishing or steering of the frame 978 as desired within the ventricle. The system 900 may advantageously allow for relatively sturdy securing or maintaining of the frame at a desired angle in order to allow for steering of the frame 978, as desired.

The system 900 may further comprise a release wire or feature 991 associated with the pivot pin feature 995. In some embodiments, the release wire 991 may be contained at least partially within the working catheter 994. The working catheter 994 may be a delivery rod, hypotube or other type of hypodermic tubing, or the like. For example, the working catheter 994 may be a relatively small-radiused tube comprising at least partially rigid material, such as metal, plastic, or the like.

The frame 978 comprises a hinge feature 977, which may be rotatably or loosely mated to the pivot pin feature 995. The wire 991 may be used to allow for disengagement of the frame 978 and hinge feature 977 from the shaft 997 associated with the working catheter 994. In some embodiments, the hinge feature 977 is configured to snap onto the pivot pin feature 995. In some embodiments, the hinge feature 977 has top and bottom portions that secure the frame 978 around the pin 995 from both the top and bottom with respect to the orientation shown in FIG. 9A. That is, although the hinge feature 977 is shown as having only a top portion that fits or rests atop the pin 995, in some embodiments, the hinge feature 977 provides full circumferential support around the pin 995. For example, the hinge feature 977 may comprise an aperture or hole through which the pin 995 may be disposed to hold the hinge loosely secured about the pin 995. The geometry of the hinge feature 977 may advantageously be designed or configured such that the frame 978 is loosely secured to the working catheter shaft 997 when the pin 995 is engaged therewith, such that the frame 978 does not come off, or become disconnected from, the shaft 997 while the frame 978 is being articulated or positioned. The shaft or groove member 997 may work in connection with a tongue member 996 to provide the actuation of the frame 978. For example, as shown in the side view of the assembly 900 shown in FIG. 9B, the tongue feature 996 may be configured to engage with an extension feature 979 of the frame such that the frame 978 is engaged with both the tongue feature 996 via the engagement feature 998 thereof, as well as the shaft/groove feature 997 via the pin 995. Therefore, relative movement between the tongue 996 and the shaft 997 may cause the frame 978 to be rotated about the pivot pin 995 and/or hinge feature 977. In some embodiments, as shown, the frame engagement feature 998 of the tongue 996 may comprise a slot or other feature configured to receive the extension 979 of the frame and allow for the application of force (e.g. downward force with respect to the orientation shown in FIG. 9B) thereto.

In some embodiments, the pull wire feature 991, when pulled or otherwise actuated or manipulated, may cause the pin 995 to become disengaged to some degree from the frame 978 and/or hinge feature 977, such that the frame 978 may be released from the catheter assembly 994. The shaft member 997 of the catheter assembly 994 may be disposed at least partially within the catheter 994.

Figure 10:
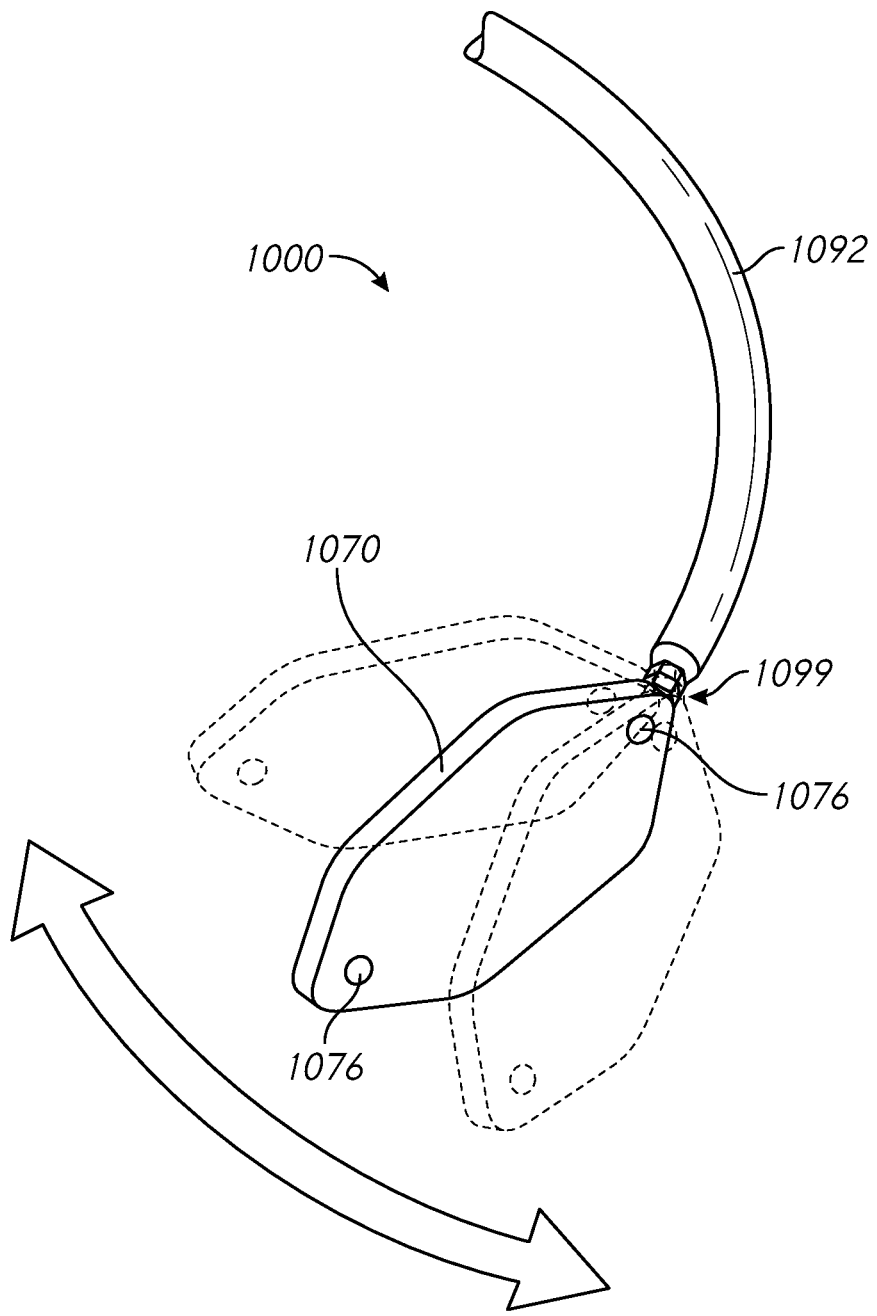
FIG. 10 illustrates a tissue adjustment pad articulation system in accordance with one or more embodiments.

FIG. 10 illustrates a papillary muscle approximation pad delivery system 1000 in accordance with one or more embodiments. The system 1000 shows articulation of a pad 1070 having a cover in accordance with embodiments of the present disclosure. The system 1000 includes a shaped and steerable pad delivery catheter 1092. The delivery catheter 1092 may have associated therewith one or more articulation mechanisms 1099, which may be used to articulate the pad 1070 for placement of the pad at a target location, such as at or near a papillary muscle or other anatomy of a ventricle of a heart. The articulation mechanism 1099 may advantageously allow for pivoting movement of the pad 1070 about one or more axes. For example, in some embodiments, the articulation mechanism 1099 may allow for rotation about a pivot point within a vertical plane of the pad 1070, such that the pad may be torqued or rotated up and down with respect to a vertical orientation of the pad. Additionally or alternatively, the articulation mechanism 1099 may provide for movement from side-to-side, such as in a direction generally orthogonal to a face or contact surface 1001 of the pad 1070. Such side-to-side articulation may allow for navigation and placement of the pad 1070 against a backside of the papillary muscle, for example. In some embodiments, side-to-side movement may be achievable at least in part by applying a force or torque to the delivery catheter 1092, or portion thereof. Such force/torque to the catheter 1092 may facilitate navigation of the shaft of the catheter and may allow for positioning thereof behind a papillary muscle, or thereabouts. By applying force or torque to the catheter 1092, the pad 1070 may be able to be fished around papillary muscle(s) or other anatomy to the desired target location.

Figure 11:
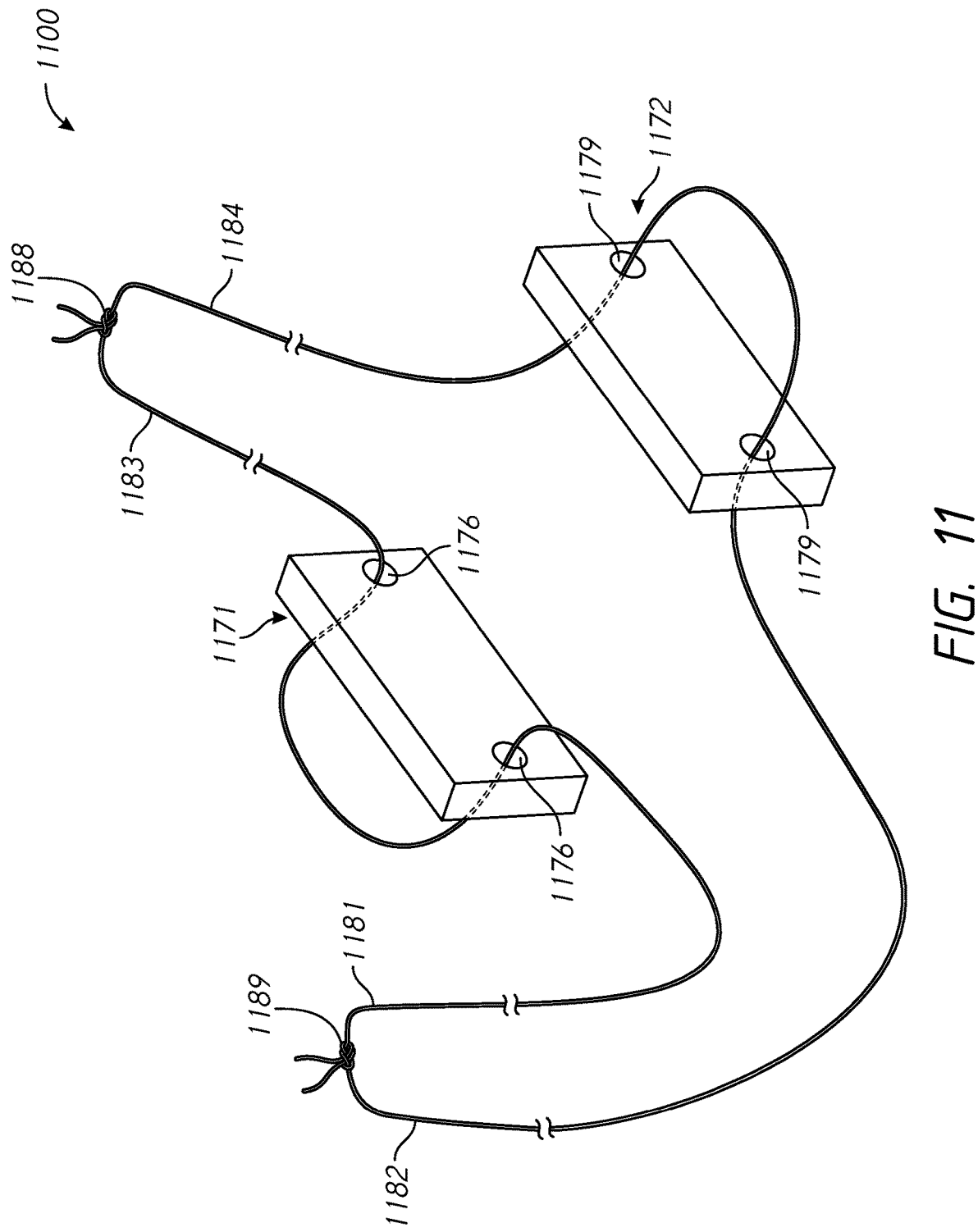
FIG. 11 illustrates a tissue adjustment pad assembly in accordance with one or more embodiments.

FIG. 11 illustrates a pad approximation system 1100 comprising two or more tissue-contact pads 1171, 1172. The diagram of FIG. 11 illustrates concepts related to the tensioning of pad devices to one another and/or suture(s), or the like. In the illustrated embodiment, a suture portion 1183 associated with a first pad 1171 is coupled or secured in some manner to a suture portion 1184 that is coupled to or otherwise associated with a second pad 1172. For example, the suture portions 1183, 1184 may be tied together, or secured with a locking mechanism, such as a clip, clasp, latch, buckle, slide, or the like. A knot 1188 is shown as coupling the suture portions 1183 and 1184. However, should be understood that suture portions coupling tissue contact pads in accordance with embodiments of the present disclosure may be coupled or secured in any suitable or desirable manner, or using any suitable or desirable mechanism or device. The suture lines may be threaded through suture holes in the pads, as shown.

In some implementations, the tissue-contact pads 1171, 1172 may be implanted and/or positioned at respective target locations in the body of a patient, such as behind the papillary muscles of the heart of the patient. The suture portions 1183, 1184 may be contained at least partially within a delivery catheter or sheath used in delivering the pads 1171, 1172 to the target locations. In some implementations, the tying or fixing of the knot or other coupling or securing feature of the suture portions 1183, 1184 may be performed or executed at least partially outside of the body of the patient, such as through a catheter access point used in the relevant surgical operation. Once the coupling 1188 has been executed outside of the body, such coupling 1188 may be brought proximate to the pads 1171, 1172 by pulling on one or more suture portions 1181, 1182, which may be associated with opposite sides or other portions of the pads 1171, 1172.

Once the coupling 1188 has been executed, the suture portion(s) 1181, 1182 may be pulled to provide tension between the pads 1171, 1172, thereby drawing the pads in a direction generally towards one another. For example, such action may be performed in order to draw the papillary muscles contacting the respective pads 1171, 1172 towards one another to provide valve correction functionality as described in detail herein. With the first coupling 1188 pulled proximate to the pads 1171, 1172, the other suture portions 1181, 1182 may likewise be coupled or secured in a manner as to maintain the desired tension between the pads 1171, 1172. Such coupling may involve drawing a slide or other locking mechanism over the suture portions 1181 1182 to a portion thereof generally proximate to the pads 1171, 1172, wherein such mechanism may be cinched or locked in order to hold the desired tension between the pads. In some implementations, the suture portions 1181, 1182 may be tied together to form a knot 1189, as shown, which may be performed locally at the target location in the patient's body, or outside of the patient's body.

In some embodiments, the suture portions are coupled to the pad devices 1171, 1172 via suture hole features 1176, 1179, or the like. Although suture holes are shown, it should be understood that any suture securing means or mechanism/component may be used to adjustably hold the sutures to the pads. Although the sutures are shown as being threaded through two suture holes of the pads, it should be understood that a single suture or suture portion may be threaded through only a single suture hole or feature of a pad, as shown in FIGS. 5A and 5B, described above.

Figure 12:
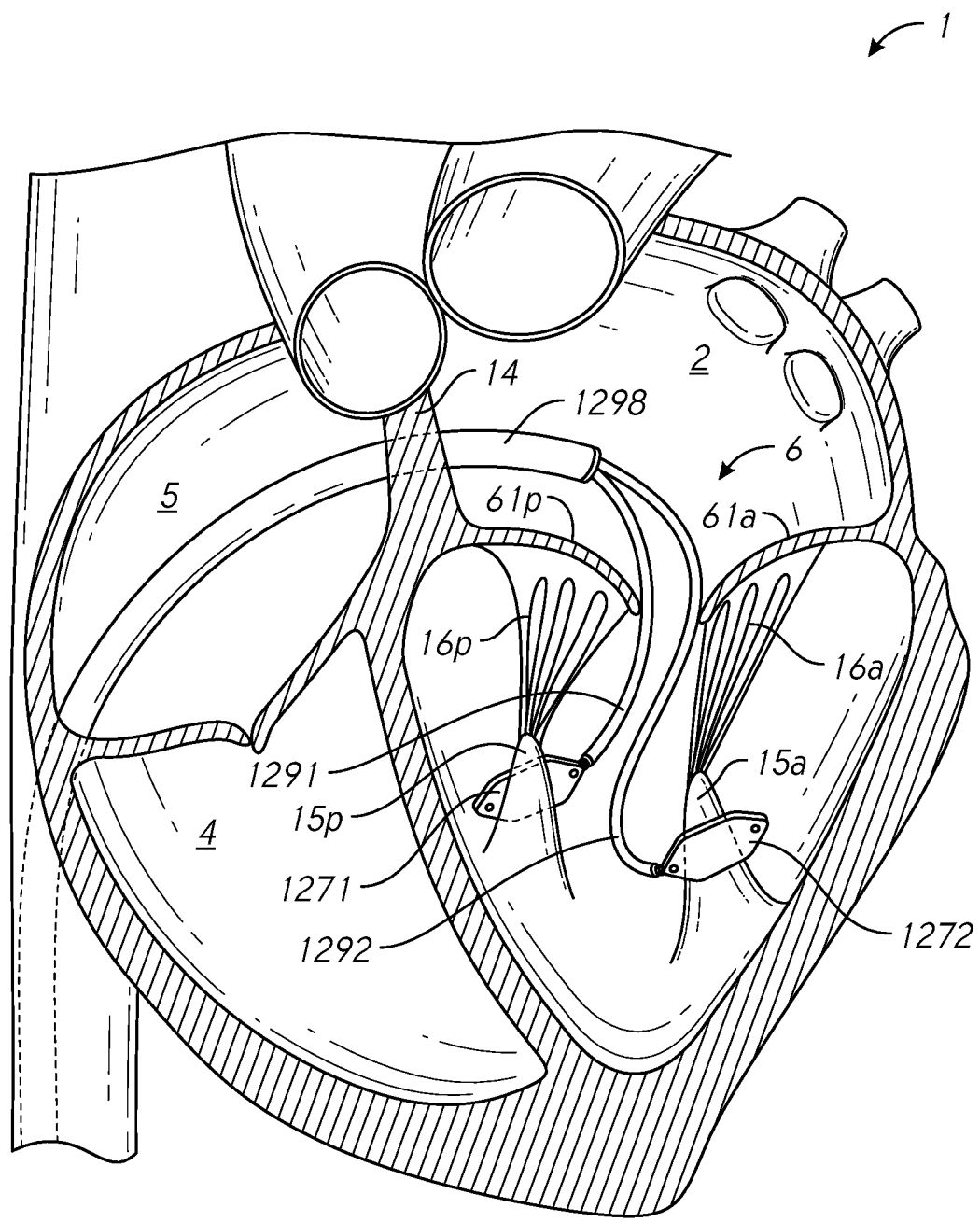
FIG. 12 illustrates a delivery system for a papillary muscle adjustment system in accordance with one or more embodiments.

FIG. 12 illustrates a delivery system 1200 for a papillary muscle adjustment system in accordance with one or more embodiments. FIG. 12 illustrates a heart 1 having positioned therein a plurality of papillary muscle approximation pads 1271, 1272, which are navigated to their respective positions behind papillary muscles using respective delivery catheters 1291, 1292. The delivery catheters 1291, 1292 may be provided to the target ventricle 3 and/or atrium 2 using a steerable sheath 1298, which may be provided to the atrium via a trans-septal procedure through one or more blood vessels of the patient and through the interatrial septum 11. The delivery catheters 1291, 1292 may be at least partially steerable to allow for navigation of the pads 1271, 1272 to their respective target locations.

The pads 1271, 1272 may be articulating pads, such that, through use of one or more articulation mechanisms or tools associated with the catheters 1291, 1292, the pads 1271, 1232 may be rotated, turned or adjusted relative to the catheters, as described in detail herein. Once provided to their target locations, the pads 1271, 1272 may be tensioned and/or drawn towards one another using one or more sutures (not shown), as described herein. By suturing and/or tensioning the implanted/positioned pads 1271, 1272 to one another, the distance between the papillary muscles may be reduced such that the papillary muscles are approximated to one another. Such approximation of the papillary muscles may advantageously reduce tension and/or a tethering of the chordae tendineae 16*a*, 16*b* physically connecting the papillary muscles 15*p*, 15*a* to respective leaflets 61*p*, 61*a* of an associated heart valve 6.

Although two delivery catheters 1291, 1292 are illustrated in the diagram of FIG. 12, it should be understood that in certain implementations, both of the pads 1271, 1272 may be navigated to their respective target locations using a single delivery catheter, or more than two delivery catheters in some embodiments. Papillary muscle approximation in accordance with the diagram of FIG. 12 may advantageously treat valve regurgitation. For example, the pads 1271, 1272 may be deposited in the ventricle 3, and left as a permanent implant for corrective valve function in the patient.

While some embodiments are described herein as implemented using separate delivery catheters, or any type of steerable catheter elements, (e.g., delivery catheters 1291 and 1292 in FIG. 12, described above), it should be understood that embodiments of the present disclosure may be implemented using a single catheter. For example, a single catheter may be used to deploy a first pad, after which a second pad may be deployed from the catheter after repositioning thereof. In some embodiments, an individual pad may be deployed at or near a first papillary muscle using a delivery catheter, after which the pad may be detached from the delivery catheter. A newly installed pad may be subsequently advanced using the same catheter (or a different catheter) to a second papillary muscle and deployed. For example, the second pad may be installed in the catheter outside of the body. Therefore, embodiments of the present disclosure may allow for implantation of multiple papillary muscle approximation pads using a single catheter (e.g., steerable catheter element).

Figure 13:
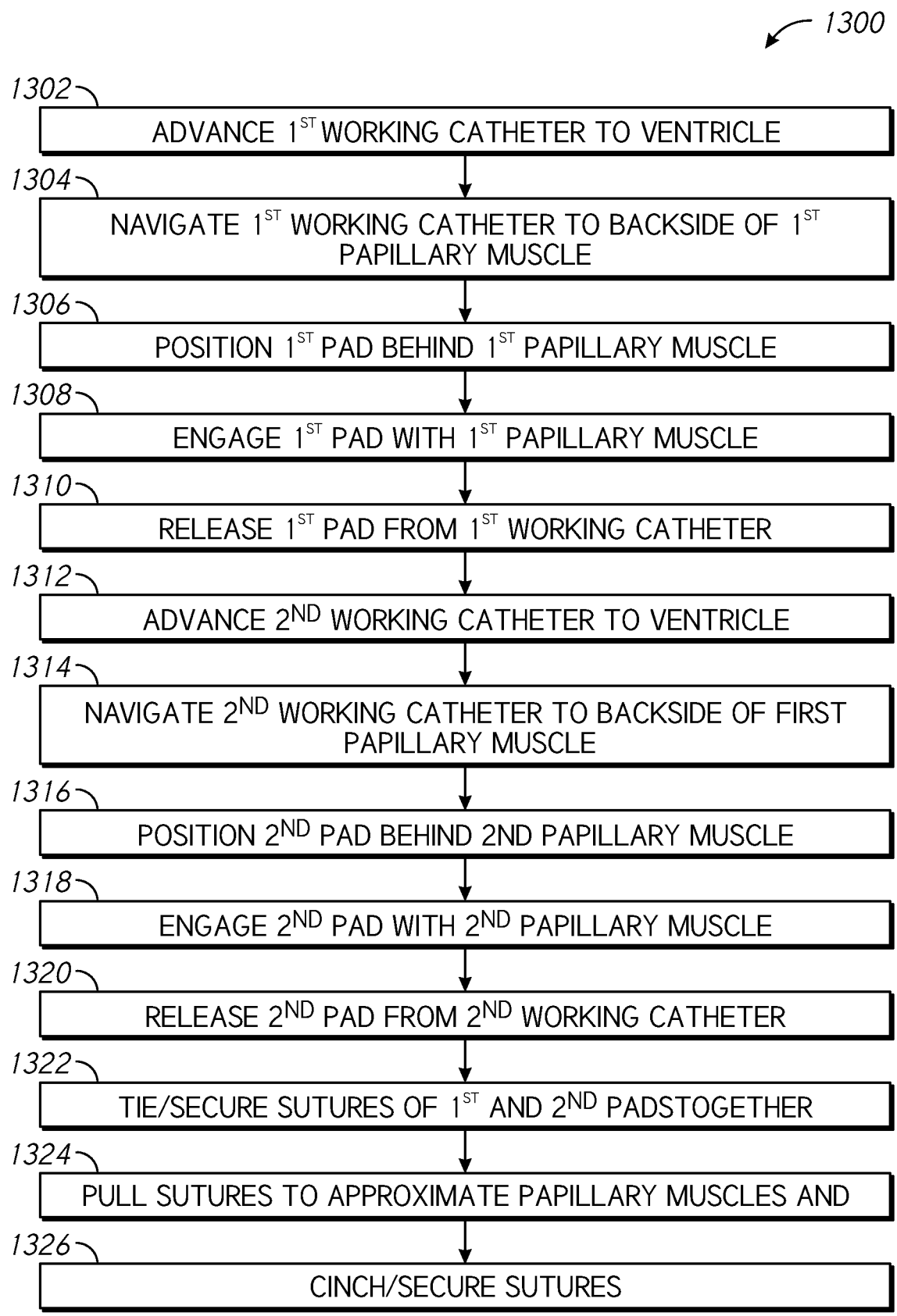
FIG. 13 is a flow diagram illustrating a process for adjusting papillary muscles in accordance with one or more embodiments.

FIG. 13 is a flow diagram illustrating a process 1300 for adjusting papillary muscles in accordance with one or more embodiments. In some implementations, the process 1300 involves navigating a steerable sheath percutaneously through an artery of a patient to the left ventricle and approximating two delivery catheters therefrom to the papillary muscles. For example, at block 1302, the process 1300 involves advancing a first working catheter to a target ventricle of the heart of the patient. In certain embodiments, the target ventricle is the left ventricle of the heart. The first working catheter may be advanced to the target ventricle using a transcatheter procedure. For example, the first working catheter may be delivered to the target ventricle using a transfemoral, transendocardial, transcoronary, transseptal, transapical, or other procedure/approach. In certain embodiments, the first working catheter may be transported within a steerable sheath. For example, the steerable sheath may comprise a distal end portion that is delivered to an atrium of the heart, wherein the first working catheter is deployed from within the sheath and through a heart valve (e.g., mitral valve) to the target ventricle.

At block 1304, the process 1300 involves navigating the first working catheter to a position proximate to a backside of a first papillary muscle of the target ventricle. In some implementations, the process involves the deployment of multiple suture-connected pledget pads, referred to herein as pad devices, behind multiple papillary muscles via percutaneous delivery. Once the pad devices are fixed to the papillary muscles, the suture(s) coupling the pad devices can be tightened so the papillary muscles are approximated or drawn together. The pad devices are advantageously implanted percutaneously, not surgically, which may be significantly less invasive and difficult to perform than surgical implantation. For example, at block 1306, the process 1300 involves deploying a first pad device from the first working catheter and positioning the first pad device behind the first papillary muscle. In some implementations, working catheter(s) used in the process 1300 have articulatable pads (e.g., the pad devices) with pledget and frame components associated therewith. The pad devices may be configured to be articulated behind the papillary muscles, and may be associated with sutures, which may be threaded through suture holes of the frames of the pad devices. The sutures may be used, as described below, to pull the pads, and therefore papillary muscles, together. In some embodiments, the first pad device may be positioned behind the first papillary muscle using a hinge feature of the first pad device and/or first working catheter, as described in detail herein. In some embodiments, the first working catheter is advanced to the target location with the first pad device already deployed therefrom or external to the distal end of the first working catheter.

At block 1308, the process involves engaging the first pad device with the first papillary muscle using one or more tissue-engagement features of the pad device, such as barbs or the like, which may be associated with a frame of the pad device, as described in detail herein. Engaging the first pad device with the first papillary muscle may be performed by manipulating or actuating a barb actuator feature associated with the first working catheter. At block 1310, the process 1300 involves releasing the first pad device from the first working catheter.

At block 1312, the process 1300 involves advancing a second working catheter to the target ventricle. The second working catheter may be advanced to the target ventricle using a transcatheter procedure in a similar manner as the first working catheter. In certain embodiments, the second working catheter may be transported within a steerable sheath. For example, the distal end portion of the steerable sheath may be delivered to an atrium of the heart, wherein the second working catheter is deployed from within the sheath and through a heart valve (e.g., mitral valve) to the target ventricle.

At block 1314, the process 1300 involves navigating the second working catheter to a position proximate to a backside of a second papillary muscle of the target ventricle. At block 1316, the process 1300 involves deploying a second pad device from the second working catheter and positioning the second pad device behind the second papillary muscle. The second pad device may be positioned behind the second papillary muscle using a hinge feature of the second pad device and/or second working catheter, as described in detail herein. In some embodiments, the second working catheter is advanced to the target location with the second pad device already deployed therefrom or external to the distal end of the second working catheter.

At block 1318, the process involves engaging the second pad device with the second papillary muscle using one or more tissue-engagement features of the pad device, such as barbs or the like, which may be associated with a frame of the pad device, as described in detail herein. Engaging the second pad device with the second papillary muscle may be performed by manipulating or actuating a barb actuator feature associated with the second working catheter. At block 1320, the process 1300 involves releasing the second pad device from the second working catheter.

At block 1322, the process involves tying, or otherwise securing, a first suture portion coupled to the first pad device to a second suture portion coupled to the second pad device. The tying or securing of the first suture portion to the second suture portion may be performed outside of the patient's body. For example, the first and second suture portions may be disposed within the first and second working catheters, respectively, and/or within a delivery sheath at least partially containing the first and second working catheters. That is, the first and second suture portions may be coupled to the first and second pad devices, respectively, within the target ventricle, and may pass through one or more blood vessels of the patient through an access opening to the outside of the patient's body, wherein the portions of the first and second suture portions that are external to the patient may be manipulated by the operating physician/technician outside of the patient's body.

At block 1324, the process 1300 involves pulling on one or more of a third suture portion coupled to the first pad device and a fourth suture portion coupled to the second pad device to thereby create tension between the first and second pad devices and approximate the first and second papillary muscles to one another.

At block 1326, the process 1300 involves cinching or securing the third suture portion to the fourth suture portion in some manner Such cinching or securing may be performed at least partially external to the patient's body. In certain embodiments, cinching or securing of the third suture portion to the fourth suture portion may involve sliding a slide or clasp feature over the third and fourth suture portions towards the first and second pad devices, to thereby draw the first and second pad devices, and associated papillary muscles, together to a desired distance or tension.

The process 1300 advantageously provides percutaneous ventricle/valve correction, which may be implemented as an alternative to, or in addition to, certain surgical approaches. For example, while papillary muscle approximation to can be performed surgically, such operations may be relatively difficult to perform and/or teach. Therefore, papillary muscle approximation using percutaneous approaches in accordance with the process 1300 may allow for access to papillary muscle approximation and other valve/ventricle treatments to an increased number of patients. Furthermore, with respect to some patients, percutaneous solutions in accordance with the present disclosure may advantageously treat the underlying cause of the relevant disease/dysfunction, that being the displacement of one or more papillary muscles.

Additional Embodiments

Depending on the embodiment, certain acts, events, or functions of any of the processes described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above but should be determined only by a fair reading of the claims that follow.

What is claimed is:

1. A method for treating a heart valve, said method comprising:
delivering first and second working catheters to a ventricle of a heart of a patient using a transcatheter procedure;
approximating a first pad associated with the first working catheter to a backside of a first papillary muscle of the ventricle;
approximating a second pad associated with the second working catheter to a backside of a second papillary muscle of the ventricle; and
manipulating one or more sutures physically coupled to at least one of the first and second pads to decrease a distance between the first and second papillary muscles;
wherein the first pad comprises a rigid frame disposed at least partially within a pledget form.

2. The method of claim 1, further comprising:
engaging the first pad with the first papillary muscle using an engagement feature of the first pad; and
engaging the second pad with the second papillary muscle using an engagement feature of the second pad.

3. The method of claim 2, wherein the engagement feature of the first pad comprises one or more barbs configured to protrude outward from the first pad and at least partially embed in tissue of the first papillary muscle.

4. The method of claim 1, wherein the frame is associated with one or more barbs that are at least partially exposed through the pledget form.

5. The method of claim 1, further comprising articulating the first pad to engage tissue of the backside of the first papillary muscle using the first working catheter.

6. The method of claim 1, further comprising delivering the first working catheter and the second working catheter to an atrium of the heart via a steerable sheath using a transseptal procedure.

7. A method comprising:
delivering first and second working catheters to a ventricle of a heart of a patient using a transcatheter procedure;

approximating a first pad associated with the first working catheter to a backside of a first papillary muscle of the ventricle;
articulating the first pad to engage tissue of the backside of the first papillary muscle using the first working catheter;
releasing the first pad from the first working catheter using a release wire associated with the first working catheter;
approximating a second pad associated with the second working catheter to a backside of a second papillary muscle of the ventricle; and
manipulating one or more sutures physically coupled to at least one of the first and second pads to decrease a distance between the first and second papillary muscles.

8. The method of claim 7, wherein, prior to said releasing the first pad from the first working catheter, a frame associated with the first pad is coupled to the release wire.

9. The method of claim 8, wherein the frame is configured to be coupled to the release wire via a hinge feature.

10. The method of claim 9, wherein said articulating the first pad involves rotating the first pad about the hinge feature.

11. The method of claim 7, wherein the release wire is disposed at least partially within the first working catheter.

12. A method further comprising:
delivering first and second working catheters to a ventricle of a heart of a patient using a transcatheter procedure;
approximating a first pad associated with the first working catheter to a backside of a first papillary muscle of the ventricle;
approximating a second pad associated with the second working catheter to a backside of a second papillary muscle of the ventricle;
manipulating one or more sutures physically coupled to at least one of the first and second pads to decrease a distance between the first and second papillary muscles; and
tying the one or more sutures at a physical location external to the patient, wherein the one or more sutures are connected between the ventricle and the physical location external to the patient via a blood vessel of the patient.

13. The method of claim 12, wherein said tying the one or more sutures involves joining one or more portions of the one or more sutures at a coupling.

14. The method of claim 13, wherein the coupling is a knot.

15. The method of claim 13, further comprising pulling at least one of the one or more sutures to bring the coupling closer to the first pad and the second pad.

16. A method comprising:
delivering first and second working catheters to a ventricle of a heart of a patient using a transcatheter procedure;
approximating a first pad associated with the first working catheter to a backside of a first papillary muscle of the ventricle;
approximating a second pad associated with the second working catheter to a backside of a second papillary muscle of the ventricle; and
manipulating one or more sutures physically coupled to at least one of the first and second pads to decrease a distance between the first and second papillary muscles, the one or more sutures comprising:
a first suture threaded through a suture-holding feature of the first pad; and
a second suture threaded through a suture-holding feature of the second pad.

17. The method of claim 16, further comprising tying a first end of the first suture to a first end of the second suture.

18. The method of claim 17, wherein said tying the first end of the first suture to the first end of the second suture is performed outside of a body of the patient.

19. The method of claim 18, wherein said manipulating the one or more sutures comprises pulling one or more of a second end of the first suture and a second end of the second suture to draw the first and second papillary muscles together.

* * * * *